(12) United States Patent
Holmqvist et al.

(10) Patent No.: US 9,320,855 B2
(45) Date of Patent: *Apr. 26, 2016

(54) MEDICAMENT DELIVERY DEVICE

(75) Inventors: Anders Holmqvist, Värmdö (SE); Stefan Lööf, Sköndal (SE)

(73) Assignee: SHL Group AB, Nacka Strand (SE)

( * ) Notice: Subject to any disclaimer, the term of this patent is extended or adjusted under 35 U.S.C. 154(b) by 172 days.

This patent is subject to a terminal disclaimer.

(21) Appl. No.: 13/983,562

(22) PCT Filed: Jan. 31, 2012

(86) PCT No.: PCT/SE2012/050096
§ 371 (c)(1),
(2), (4) Date: Aug. 16, 2013

(87) PCT Pub. No.: WO2012/105898
PCT Pub. Date: Aug. 9, 2012

(65) Prior Publication Data
US 2014/0371670 A1    Dec. 18, 2014

Related U.S. Application Data

(60) Provisional application No. 61/439,001, filed on Feb. 3, 2011.

(30) Foreign Application Priority Data

Feb. 3, 2011  (SE) ........................................ 1150076

(51) Int. Cl.
*A61M 5/315* (2006.01)
*A61M 5/20* (2006.01)
*A61M 5/24* (2006.01)

(52) U.S. Cl.
CPC ............. *A61M 5/31596* (2013.01); *A61M 5/20* (2013.01); *A61M 5/2033* (2013.01);
(Continued)

(58) Field of Classification Search
CPC ..... A61M 5/284; A61M 5/2448; A61M 5/24; A61M 5/2066; A61M 5/31571; A61M 5/3158; A61M 5/31578; A61M 5/31596; A61M 2005/2073; A61M 5/20; A61M 5/2033; A61M 5/31505; A61M 5/31565; A61M 2005/2451; A61M 2005/2026

USPC ........................................................... 604/89
See application file for complete search history.

(56) References Cited

U.S. PATENT DOCUMENTS 6,793,646 B1 *  9/2004  Giambattista ....... A61M 5/2066
                                                         604/208
6,893,420 B2    5/2005  Arnisolle
(Continued)

FOREIGN PATENT DOCUMENTS

WO   2009/100550 A1   8/2009
WO   2009/147026 A1   12/2009
(Continued)

OTHER PUBLICATIONS

Sweden Patent Office, Int'l Search Report in PCT/SE2012/050096, May 8, 2012.
(Continued)

*Primary Examiner* — Theodore Stigell
*Assistant Examiner* — Amber Stiles
(74) *Attorney, Agent, or Firm* — Piedmont Intellectual Property

(57) ABSTRACT

A medicament delivery device for a reconstituted medicament, comprising a proximal housing part (12; 12"; 12'''), a distal housing part (10; 10"; 10'''), a medicament delivery drive unit and actuation means, wherein the medicament delivery drive unit is mounted in said distal housing part and wherein the actuation means further include an activation member (74; 101; 201) which is displaceable between an inactive position wherein the actuator is prevented from engaging the medicament delivery drive unit and an active position wherein the actuator is able to engage the medicament delivery drive, whereby the actuator is capable of interacting with said medicament delivery drive unit to perform a delivery of the reconstituted medicament only in the active position of the activation member and in the second position of the medicament delivery drive unit.

21 Claims, 23 Drawing Sheets

(52) U.S. Cl.
CPC .......... *A61M 5/2066* (2013.01); *A61M 5/2448* (2013.01); *A61M 5/31505* (2013.01); *A61M 5/31565* (2013.01); *A61M 2005/2026* (2013.01); *A61M 2005/2073* (2013.01); *A61M 2005/2451* (2013.01)

(56) References Cited

U.S. PATENT DOCUMENTS 8,961,455 B2 * 2/2015 Holmqvist et al. ............ 604/82
2014/0155820 A1 * 6/2014 Holmqvist et al. ............ 604/89

FOREIGN PATENT DOCUMENTS

WO    2010/003262 A1    1/2010
WO    2012/030277 A1    3/2012

OTHER PUBLICATIONS

Sweden Patent Office, Written Opinion in PCT/SE2012/050096, May 8, 2012.

* cited by examiner

MEDICAMENT DELIVERY DEVICE

FIELD OF THE INVENTION

The present invention relates to a medicament delivery device and in particular to a medicament delivery device arranged to handle medicament containers having at least two chambers for containing agents to be manually mixed before being delivered.

BACKGROUND OF THE INVENTION

There are a number of devices on the market for self-administration of drugs where the drug is stored in powder form in a medicament container. This is due to the fact that many drugs, when mixed with a diluent, tend to degenerate if stored. There is thus a growing market for so called multi-chamber medicament containers, i.e. containers having at least two chambers, where at least one chamber contains the medicament in powder form, i.e. the medicament agent, and one chamber contains the diluent agent with which the medicament is to be mixed prior to delivery.

For many devices the mixing of the medicament and the diluent is performed by manually operating a medicament delivery device such as an injection device.

One such device is disclosed in WO2009100550 where a proximal housing part is turned in relation to a distal housing part whereby the first or proximal housing part having a multi-chamber medicament container is engaged and moved into the distal housing part. This, in turn, causes a plunger rod via a first piston-like member to urge the diluent agent in one of the chambers into a second chamber through channels in the container, wherein the channels fluidly interconnect the two chambers. The medicament powder and the diluent agent are mixed into a reconstituted medicament.

To activate the delivery of the medicament, i.e. to inject the medicament, an activation member, in the form of a push button, at one end of the injector is activated. In order to prevent an activation of the device before the mixing step or process is completed, the actuation member or push button at the distal end of the device is locked by a locking member that blocks the axial movement of the push-button relative to the housing, i.e. the push-button is hindered from being pressed. At the end of the mixing sequence, the locking member is activated and moved out of its locking position. After performed mixing, a dose delivery is thus activated by manually operating the actuation member.

SUMMARY OF THE INVENTION

An object of the present invention is to obtain and deliver a reconstituted medicament in a safe and reliable way where a complete and uninterrupted mixing step of mixing a medicament agent and a diluent agent is achieved for obtaining the reconstituted medicament and where an unintentional delivery of the reconstituted medicament is avoided until the mixing step has been completely achieved.

This and other objects are achieved by providing a medicament delivery device having the features defined in the dependent claim. Exemplary embodiments of the invention are defined in the dependent claims.

According to a first aspect of the invention, there is provided a medicament delivery device comprising a proximal housing part adapted to accommodate a multi-chamber container containing at least two agents; a distal housing part connected to said proximal housing part; a medicament delivery drive unit accommodated in the distal housing part, wherein the proximal housing part and the distal housing part are configured to be movable relative to one another from an extended position to a retracted position whereby the medicament delivery drive unit acts on said multi-chamber container for mixing said at least two agents and thereby obtaining the reconstituted medicament; and actuation means provided on the distal housing part and including an actuator provided to engage the medicament delivery drive unit when operated by a user for delivering the reconstituted medicament; wherein the medicament delivery drive unit is mounted in said distal housing part so as to be moved by the proximal housing part, when the proximal and distal housing parts are moved from the extended position to the retracted position, from a first position spaced from the actuator to a second position in which said medicament delivery drive unit can be engaged by the actuator, and wherein the actuation means further include an activation member which is displaceable between an inactive position wherein the actuator is prevented from engaging the medicament delivery drive unit and an active position wherein the actuator is able to engage the medicament delivery drive, whereby the actuator is capable of interacting with said medicament delivery drive unit to perform a delivery of the reconstituted medicament only in the active position of the activation member and in the second position of the medicament delivery drive unit.

Thus, the present invention is based on the insight that by allowing said medicament delivery drive unit to be moved between the first and second position, i.e. separating the medicament delivery drive unit and the actuation means from each other, a complete mixing is ensured before a delivery of the reconstituted medicament can be performed. Furthermore, due to the distance between the medicament delivery drive unit and the activation means an accidental delivery is avoided.

BRIEF DESCRIPTION OF THE DRAWINGS

In the following detailed description of the invention, reference will be made to the accompanying drawings, in which.

DETAILED DESCRIPTION OF THE INVENTION OF THE INVENTION

Figure 1:
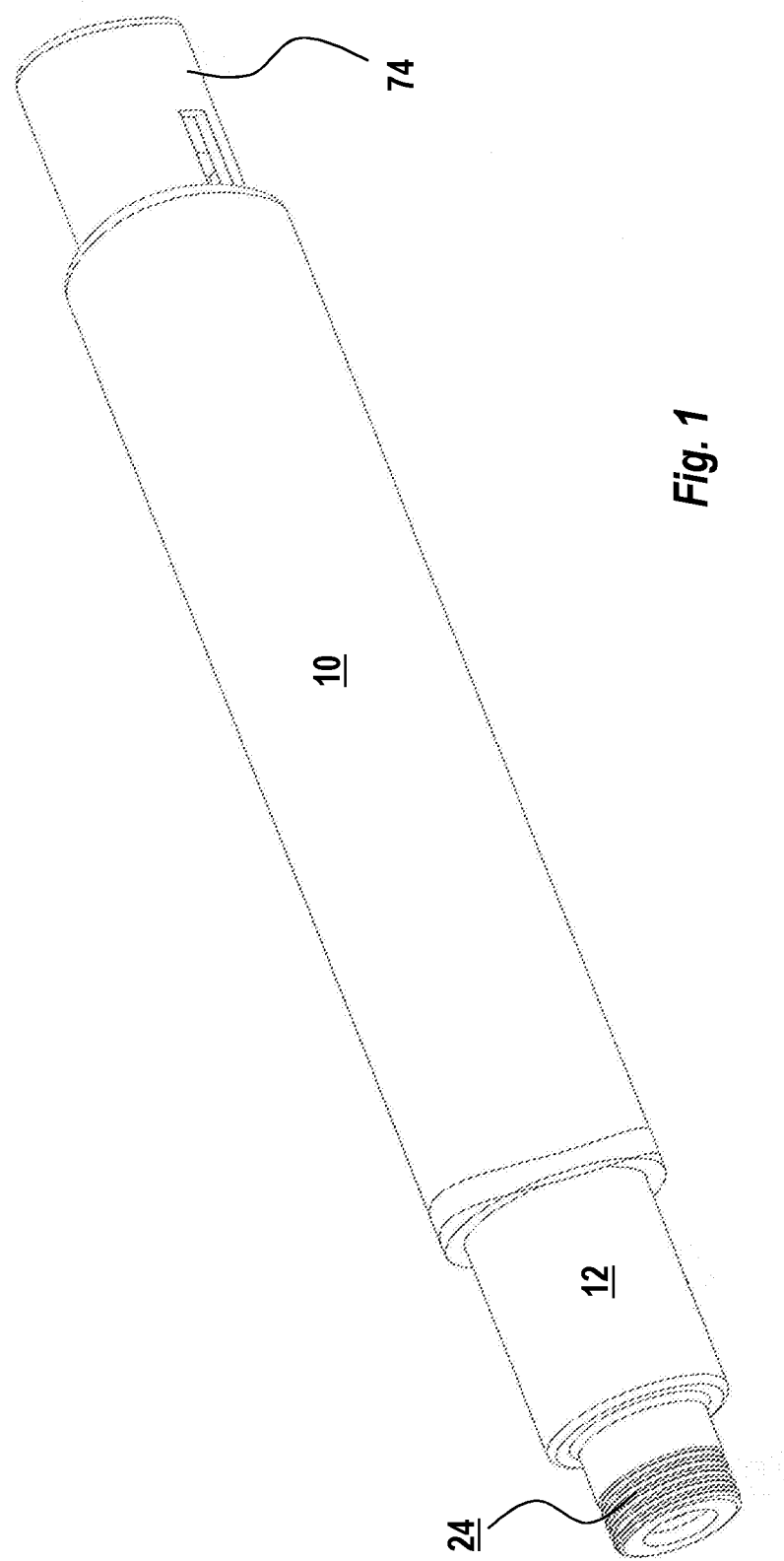
FIG. 1 is a perspective view of a medicament delivery device according to a first embodiment of the invention.

In the present application, when the term "distal part/end" is used, this refers to the part/end of the medicament delivery device, or the parts/ends of the members thereof, which is/are located the furthest away from the medicament delivery site. Correspondingly, when the term "proximal part/end" is used, this refers to the part/end of the medicament delivery device, or the parts/ends of the members thereof, which, is/are located closest to the medicament delivery site.

Furthermore, it should be noted that the term "axial" or "axially" as used herein is intended to refer to a direction along the central axis of the medicament delivery device when assembled. In other words, the central axis extends through the medicament delivery device along the direction in which a proximal and a distal housing parts are movable and connected together. Thus, the central axis extends in the direction in which the medicament is delivered. It should also be noted that the term "distally" as used herein is intended to refer to a direction along the central axis of the medicament delivery device towards the distal end of the device i.e. towards the part/end of the medicament delivery device which is located the furthest away from the medicament delivery site, and the term "proximally" as used herein is intended to refer to a direction along the central axis of the medicament delivery device towards the proximal end of the device, i.e. towards the part/end of the medicament delivery device which is located closest to the medicament delivery site.

Moreover, in the second embodiment, the same components or features as for the first embodiment have the same reference numerals but with a double apostrophe "; and in the third embodiment, the same components or features as for the first embodiment have the same reference numerals but with a triple apostrophe '''.

The medicament delivery device in the present invention comprises a proximal housing part 12; 12'; 12''' adapted to accommodate a multi-chamber container 22; 22'; 22''' containing at least two agents; a distal housing part 10; 10"; 10''' connected to said proximal housing part; a medicament delivery drive unit accommodated in the distal housing part, wherein the proximal housing part and the distal housing part are configured to be movable relative to one another from an extended position to a retracted position whereby the medicament delivery drive unit acts on said multi-chamber container for mixing said at least two agents and thereby obtaining the reconstituted medicament; and actuation means provided on the distal housing part and including an actuator 74; 74"; 74''' provided to engage the medicament delivery drive unit when operated by a user for delivering the reconstituted medicament; wherein the medicament delivery drive unit is mounted in said distal housing part so as to be moved by the proximal housing part, when the proximal and distal housing parts are moved from the extended position to the retracted position, from a first position spaced from the actuator to a second position in which said medicament delivery drive unit can be engaged by the actuator, and wherein the actuation means further include an activation member 74; 101; 201 which is displaceable between an inactive position wherein the actuator is prevented from engaging the medicament delivery drive unit and an active position wherein the actuator is able to engage the medicament delivery drive, whereby the actuator is capable of interacting with said medicament delivery drive unit to perform a delivery of the reconstituted medicament only in the active position of the activation member and in the second position of the medicament delivery drive unit.

Figure 2:
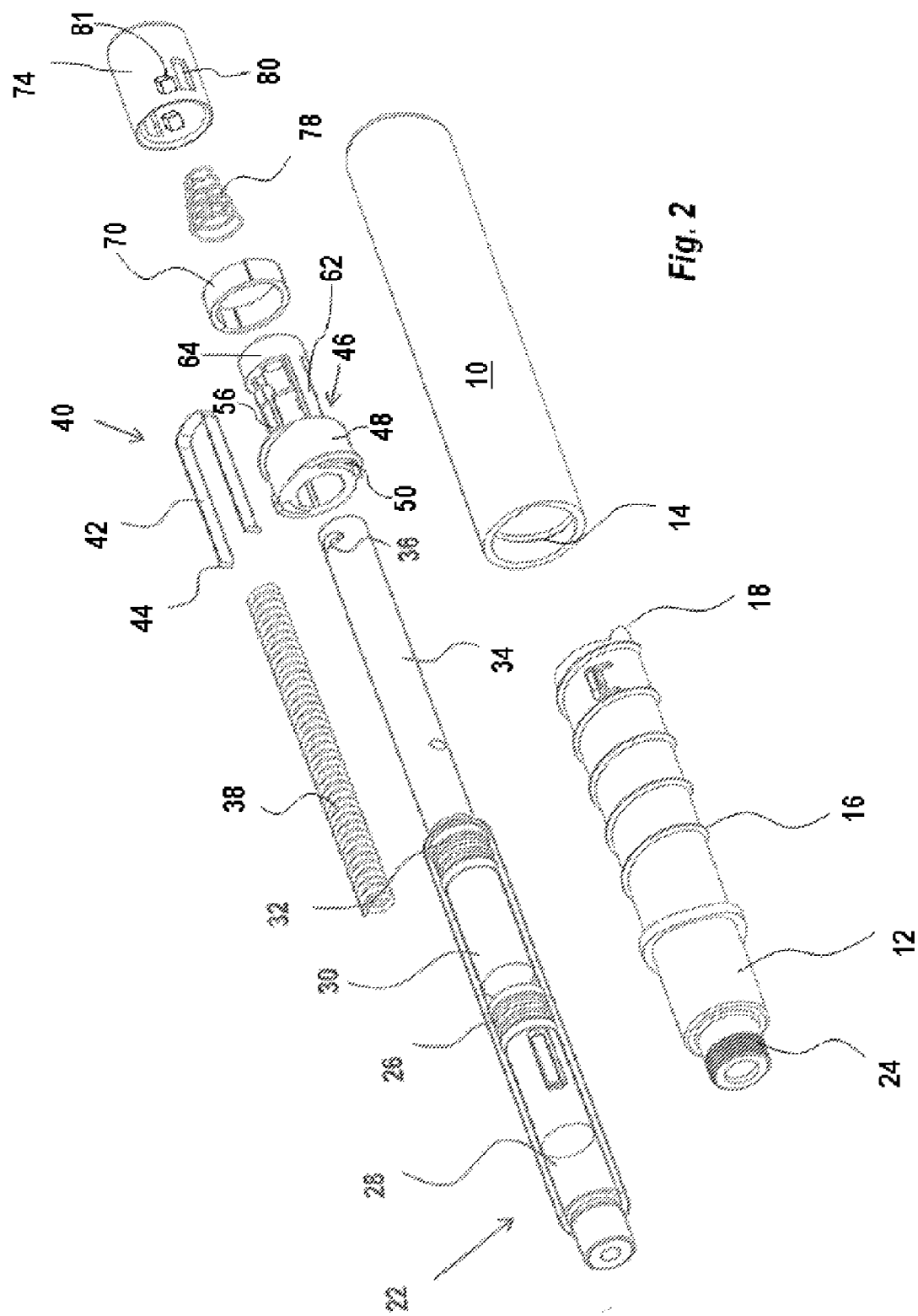
FIG. 2 is an exploded view of the device of FIG. 1, FIGS. 3 to 4 are detailed views of components comprised in the embodiment of FIG. 1, FIGS. 5 to 7 are detailed views of different functional positions of the device of FIG. 1.
Figure 3:
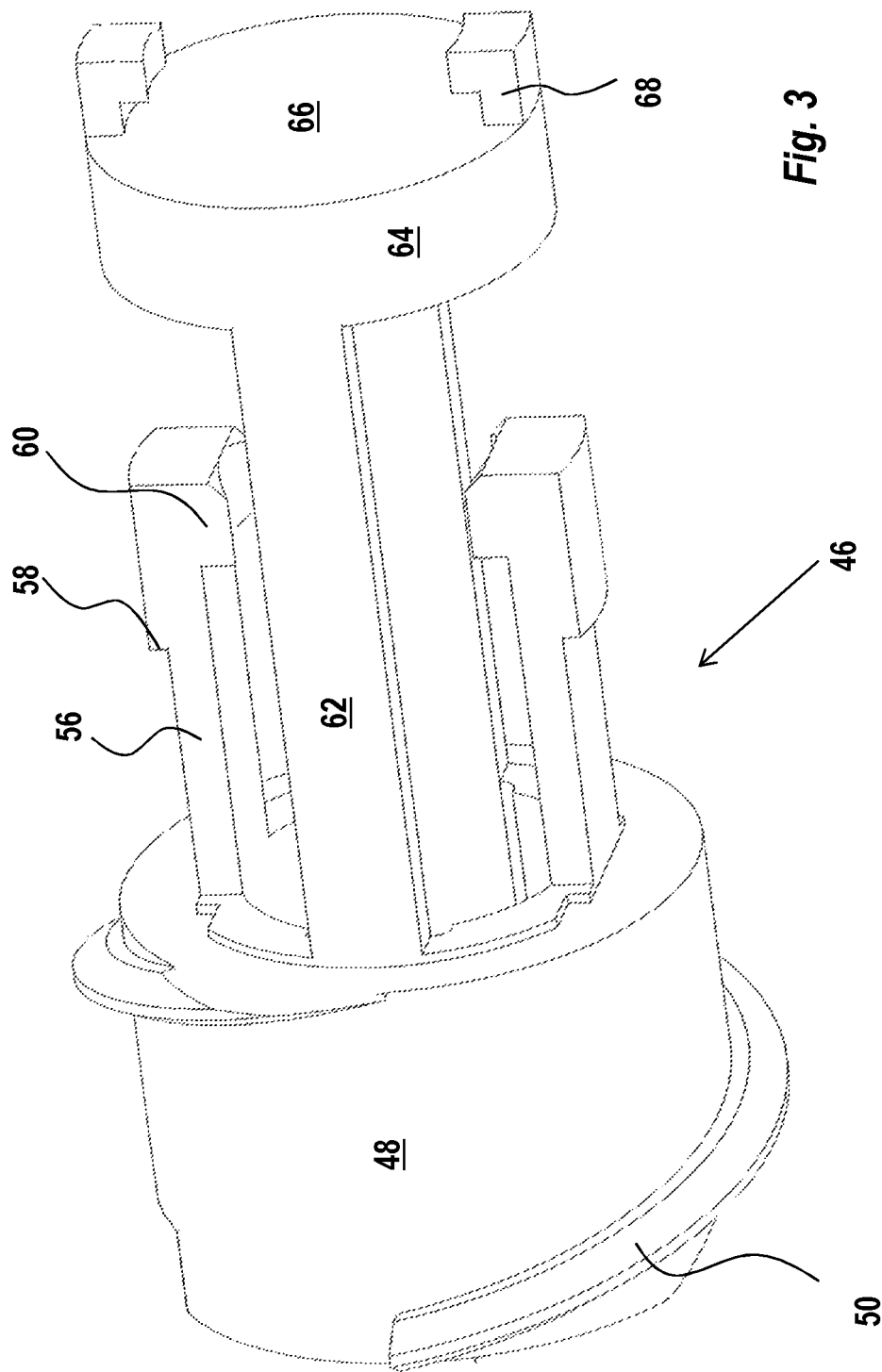
Figure 4:
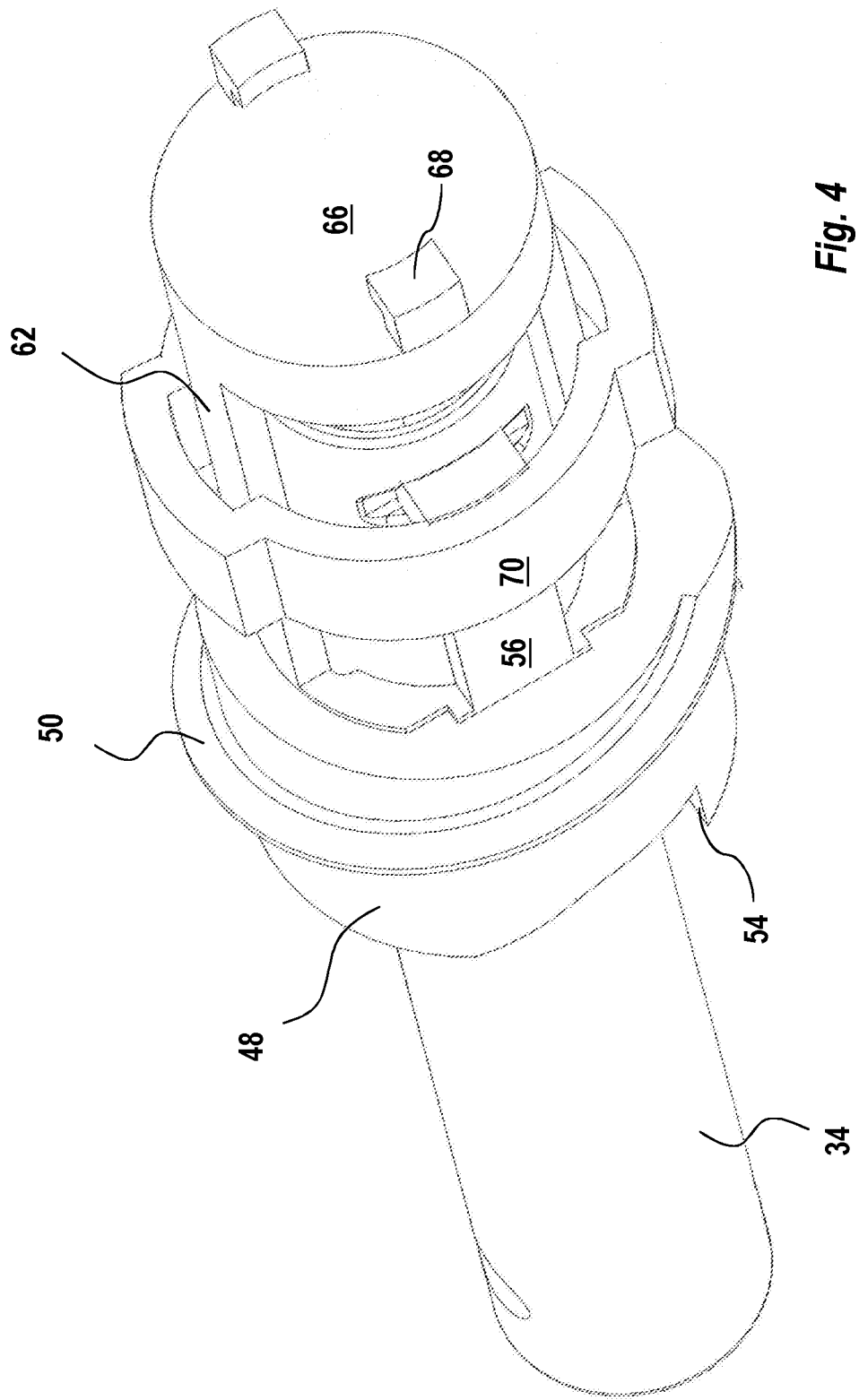
Figure 5:
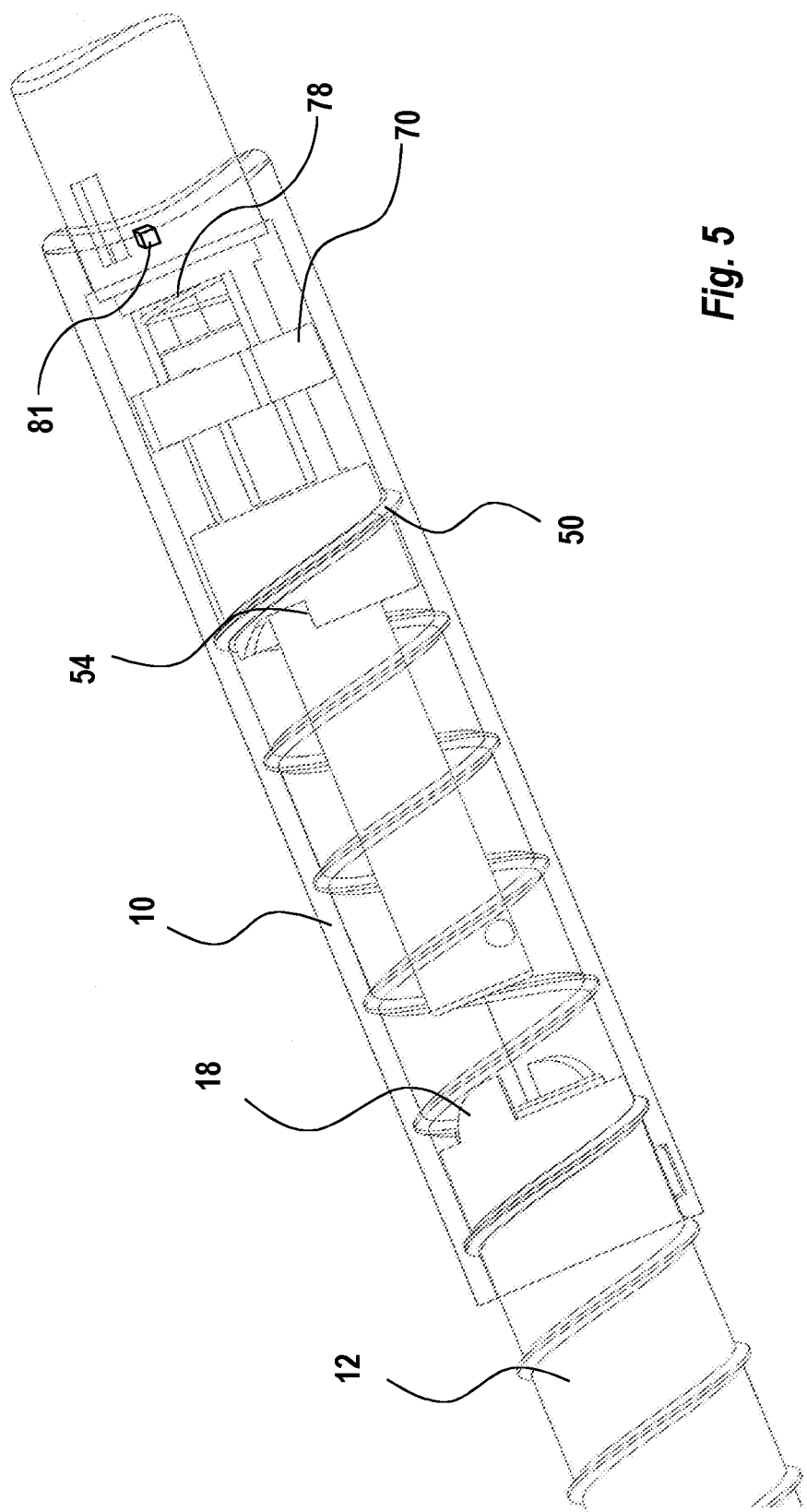
Figure 6:
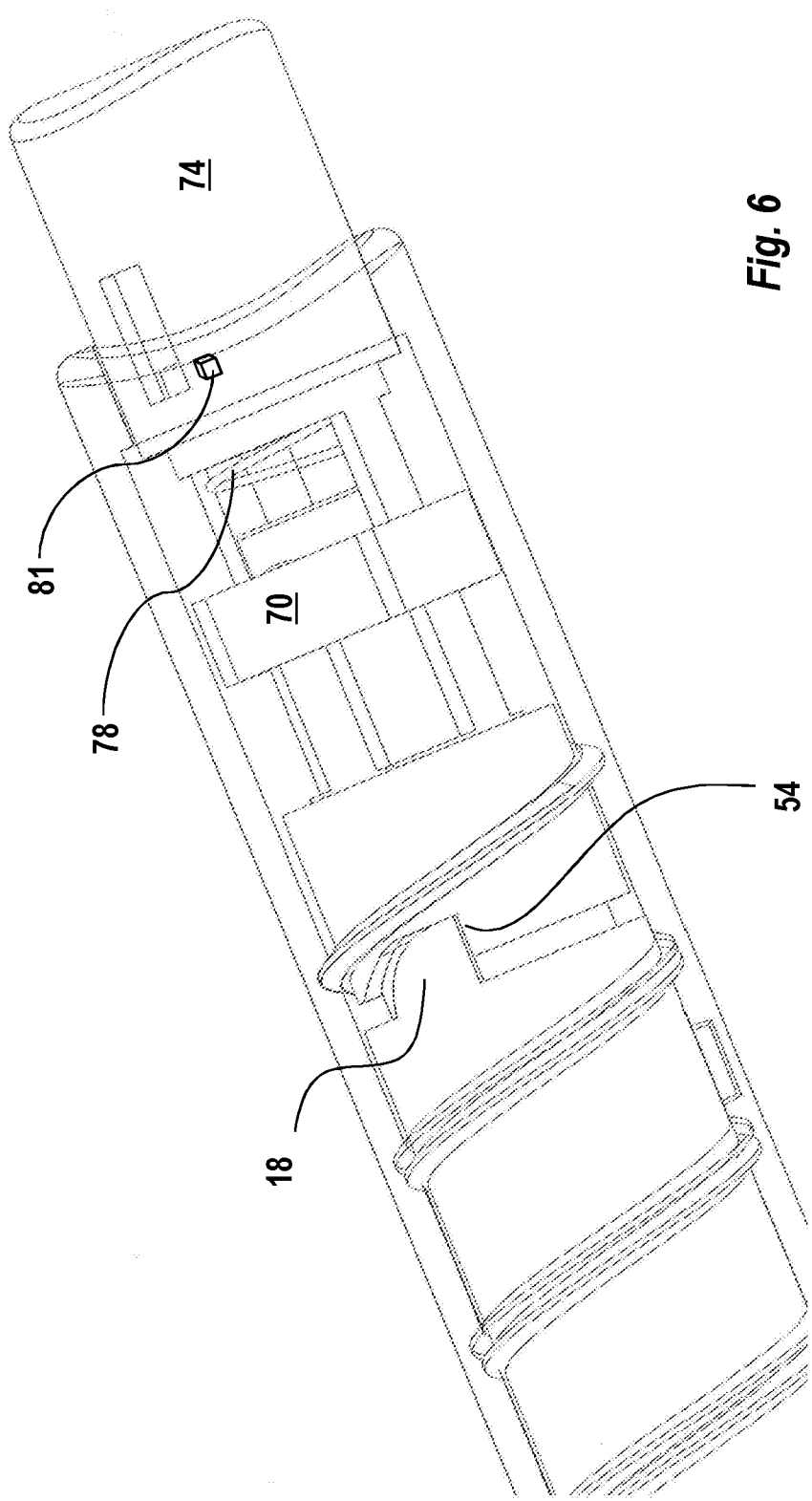
Figure 7:
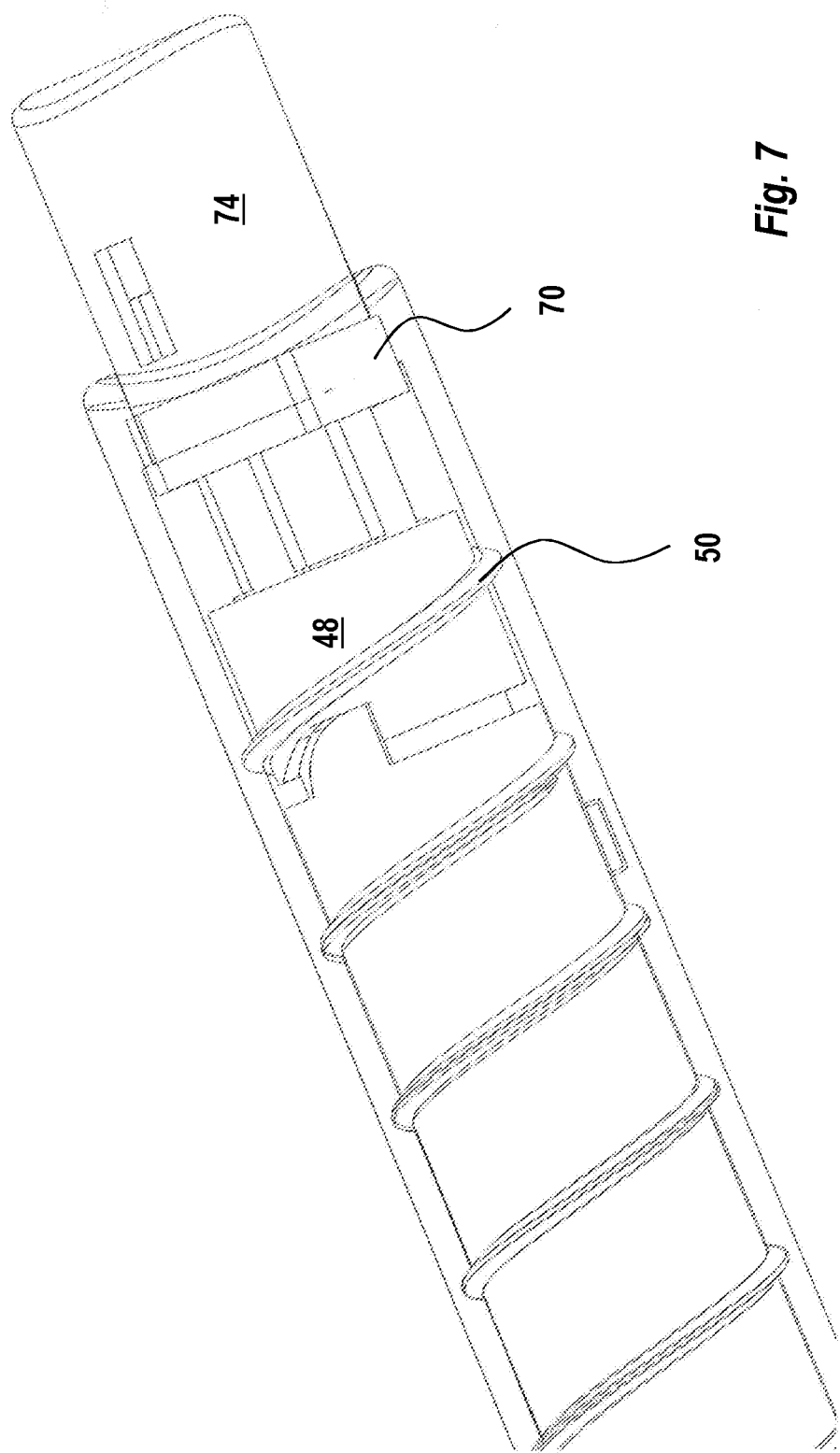

FIGS. 1 to 7 show a first embodiment of the present invention, where FIG. 1 is a perspective view of the medicament delivery device according to the first embodiment of the invention and FIG. 2 is an exploded view of the device of FIG. 1. FIGS. 3 and 4 are detailed views of some components of the device of FIG. 1. In FIG. 4, the connection member 46 is shown when connected to a spring-loaded plunger rod 34. In FIG. 5 is shown when the proximal and distal housing parts are in an extended position and the medicament delivery drive unit is in the first position. In FIG. 6 is shown when the proximal and distal housing parts are in a retracted position and the medicament delivery drive unit is still in the first position. In FIG. 7 is shown when the medicament delivery drive unit is in the second position.

Figure 8:
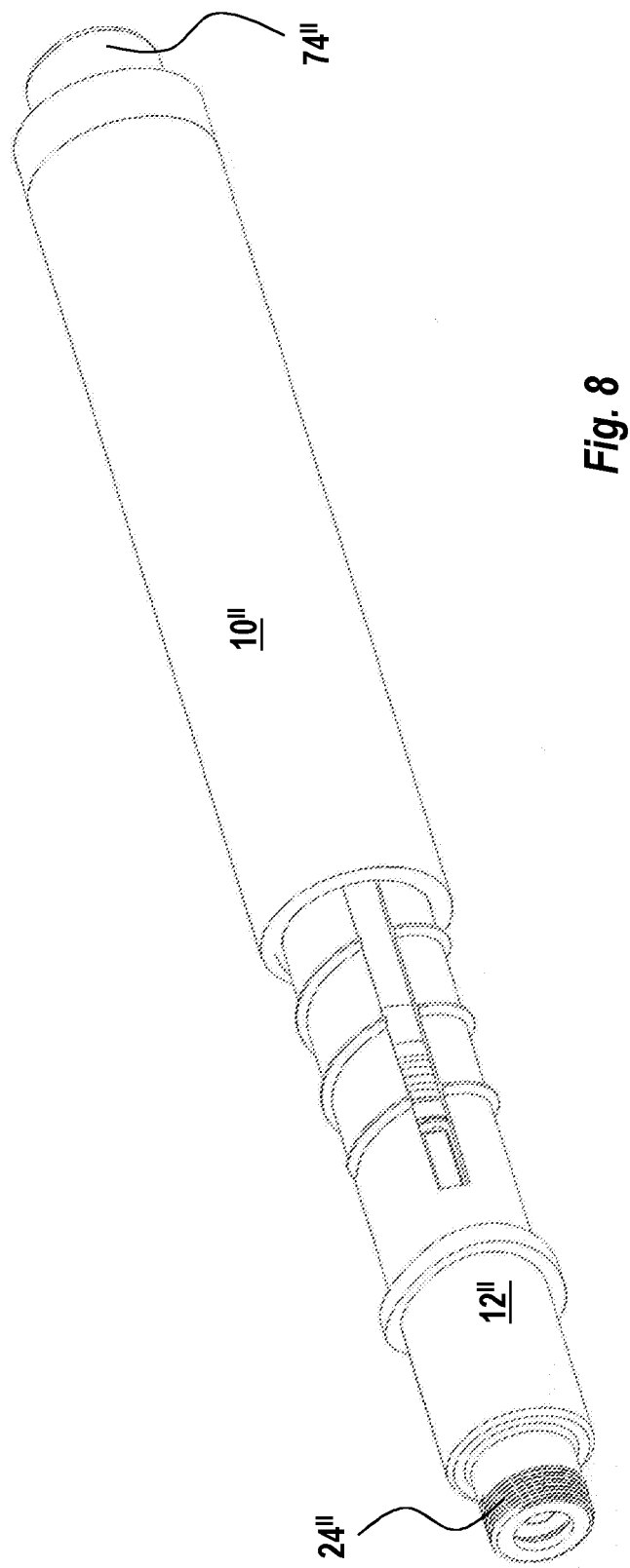
FIG. 8 is a perspective view of a medicament delivery device according to a second embodiment of the invention.
Figure 9:
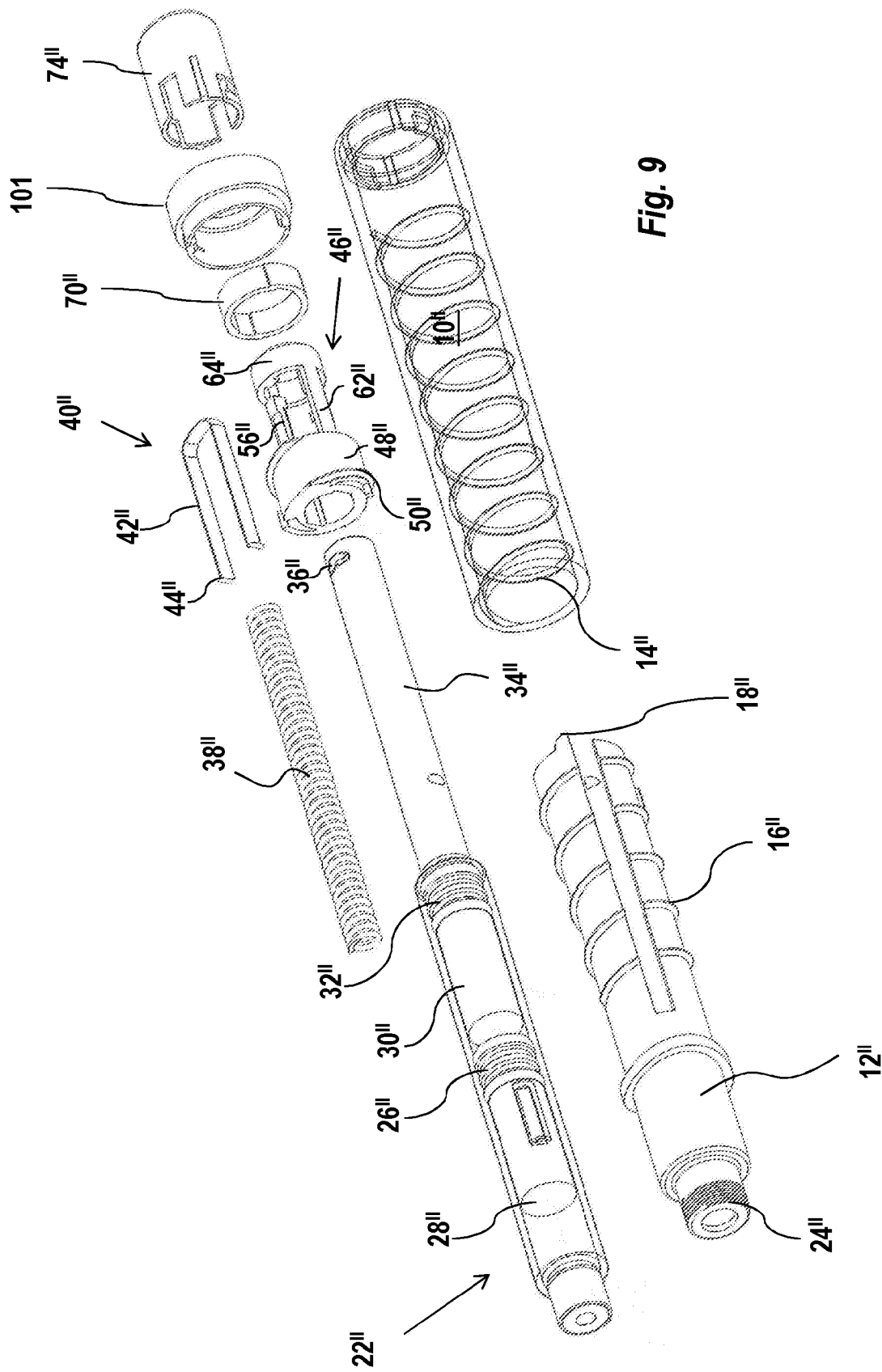
FIG. 9 is an exploded view of the device of FIG. 8, FIGS. 10-12 are detailed exploded views of components of the device of FIG. 8, FIGS. 13-14 are detailed views of different functional positions of the device of FIG. 8.
Figure 10:
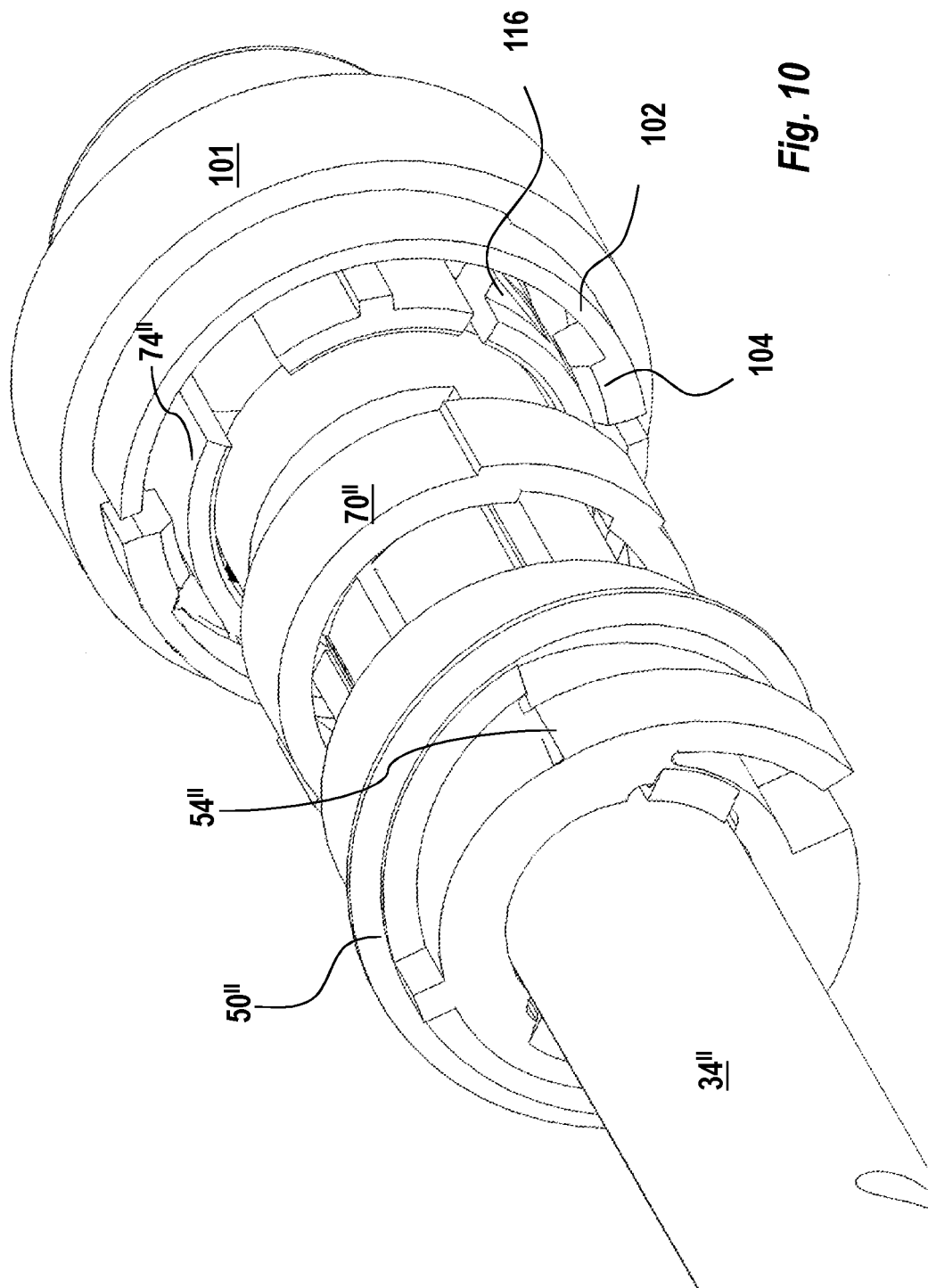
Figure 11:
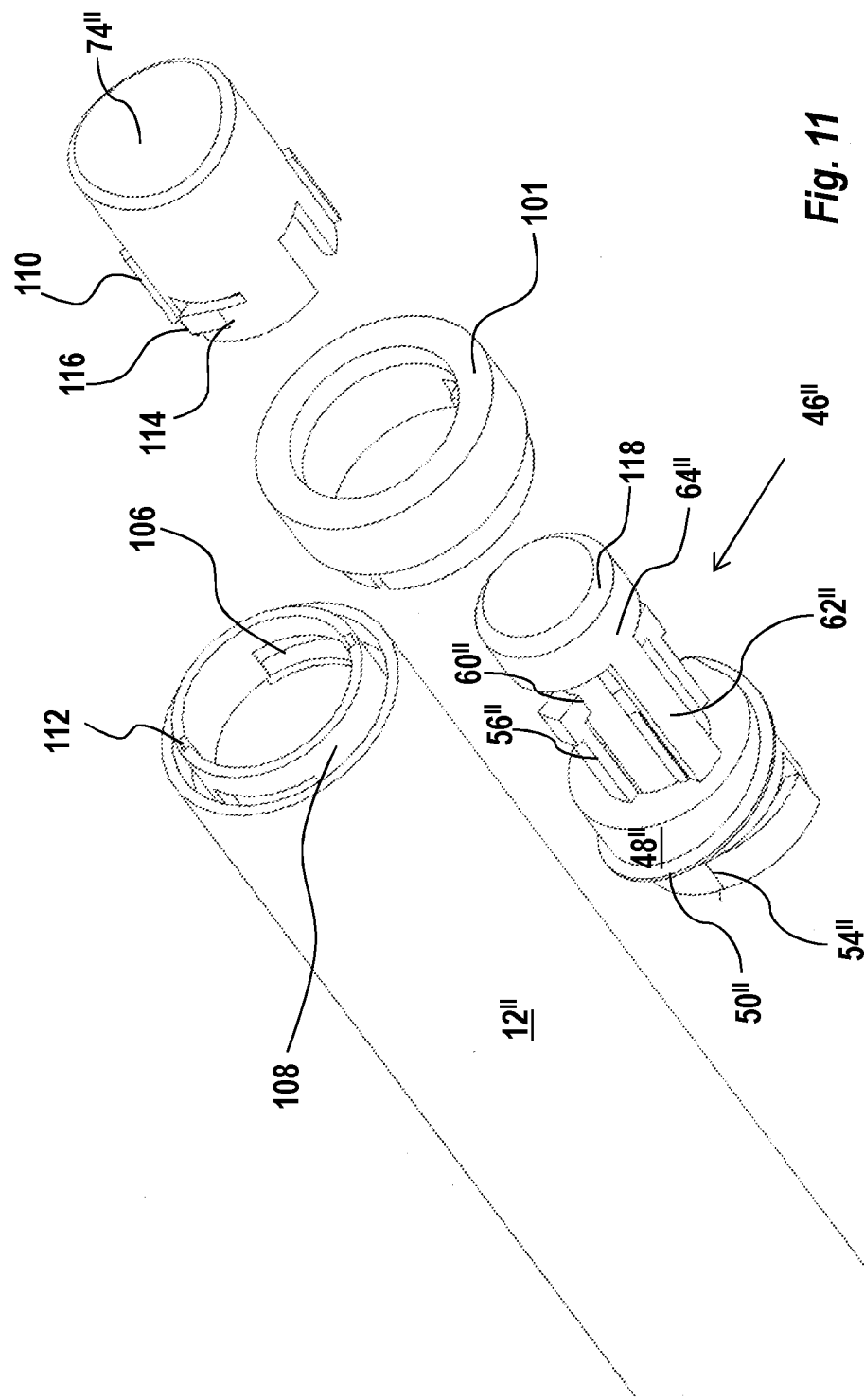
Figure 12:
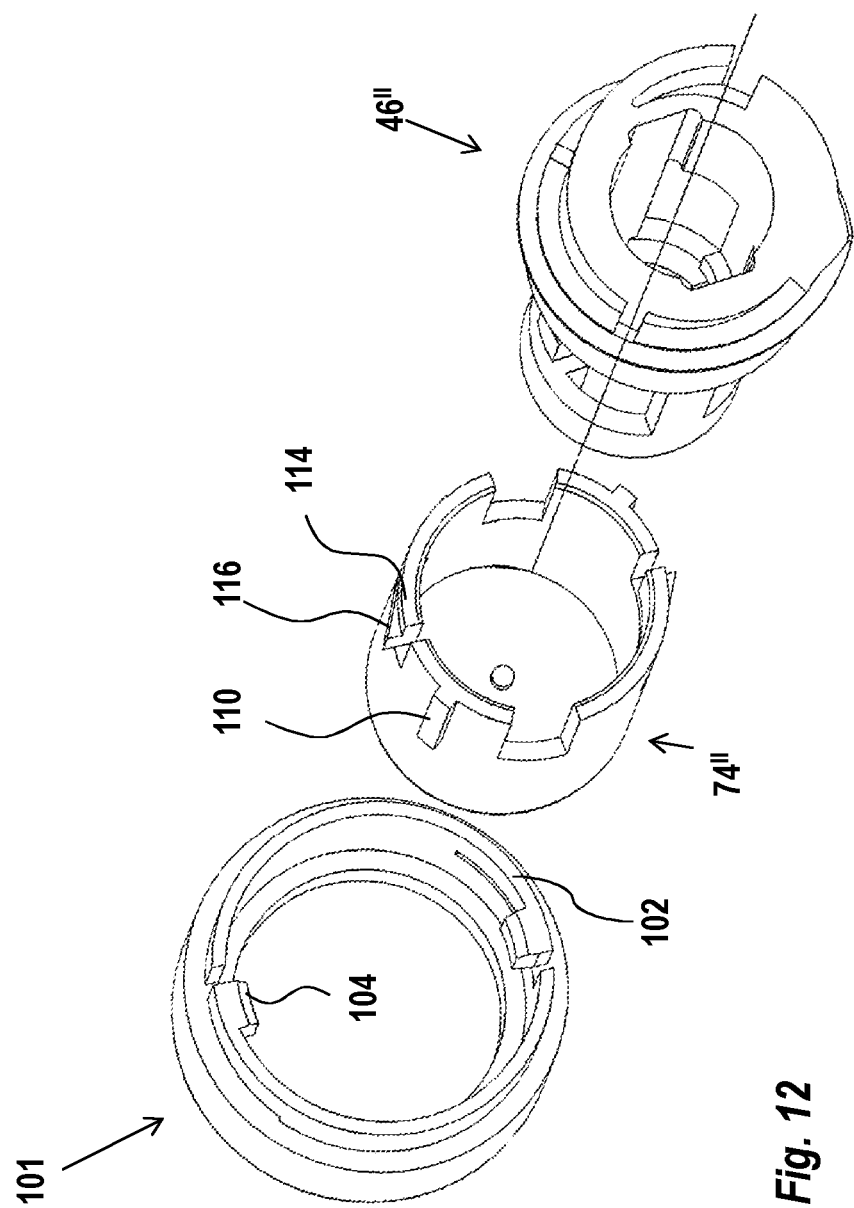
Figure 13:
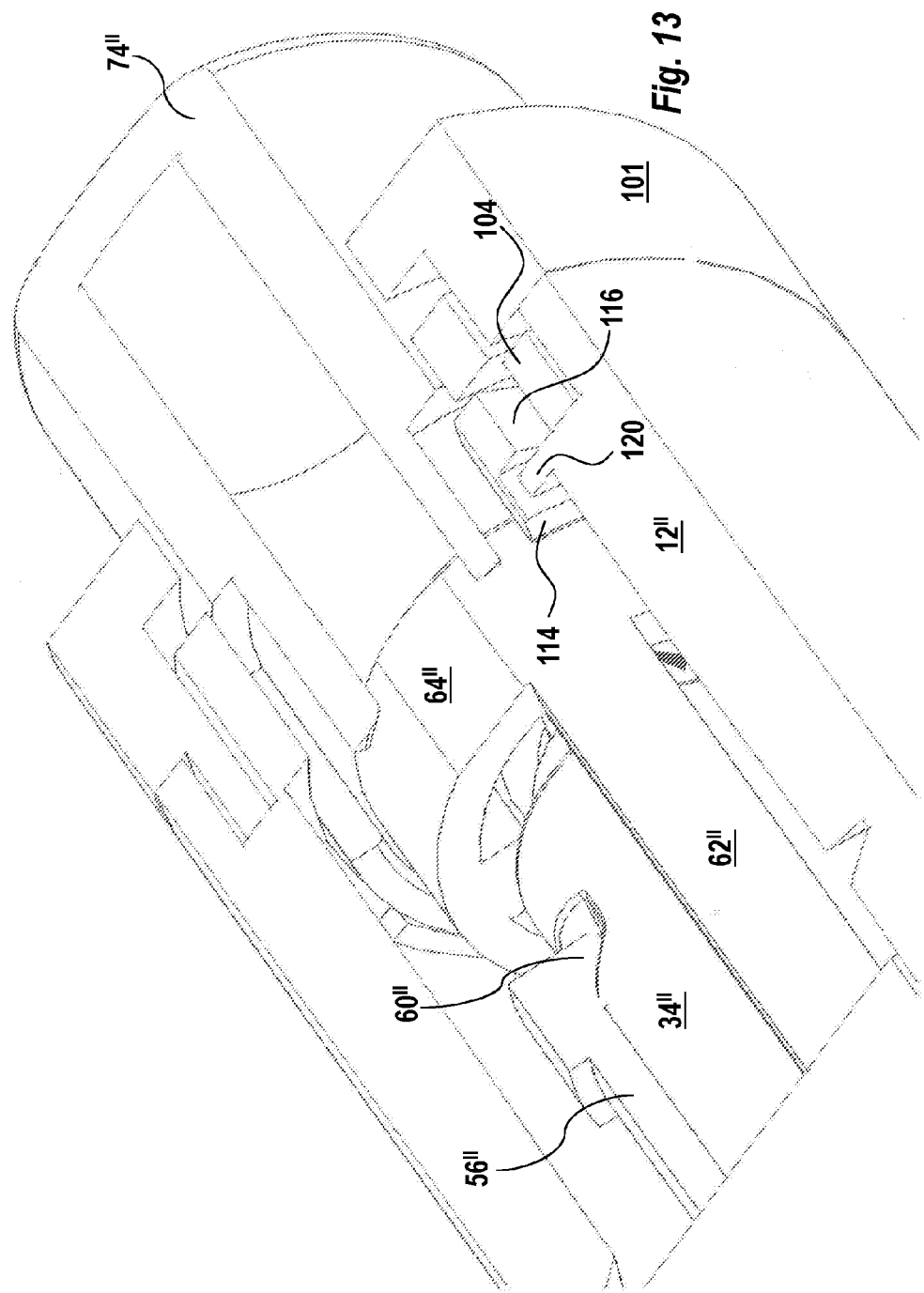
Figure 14:
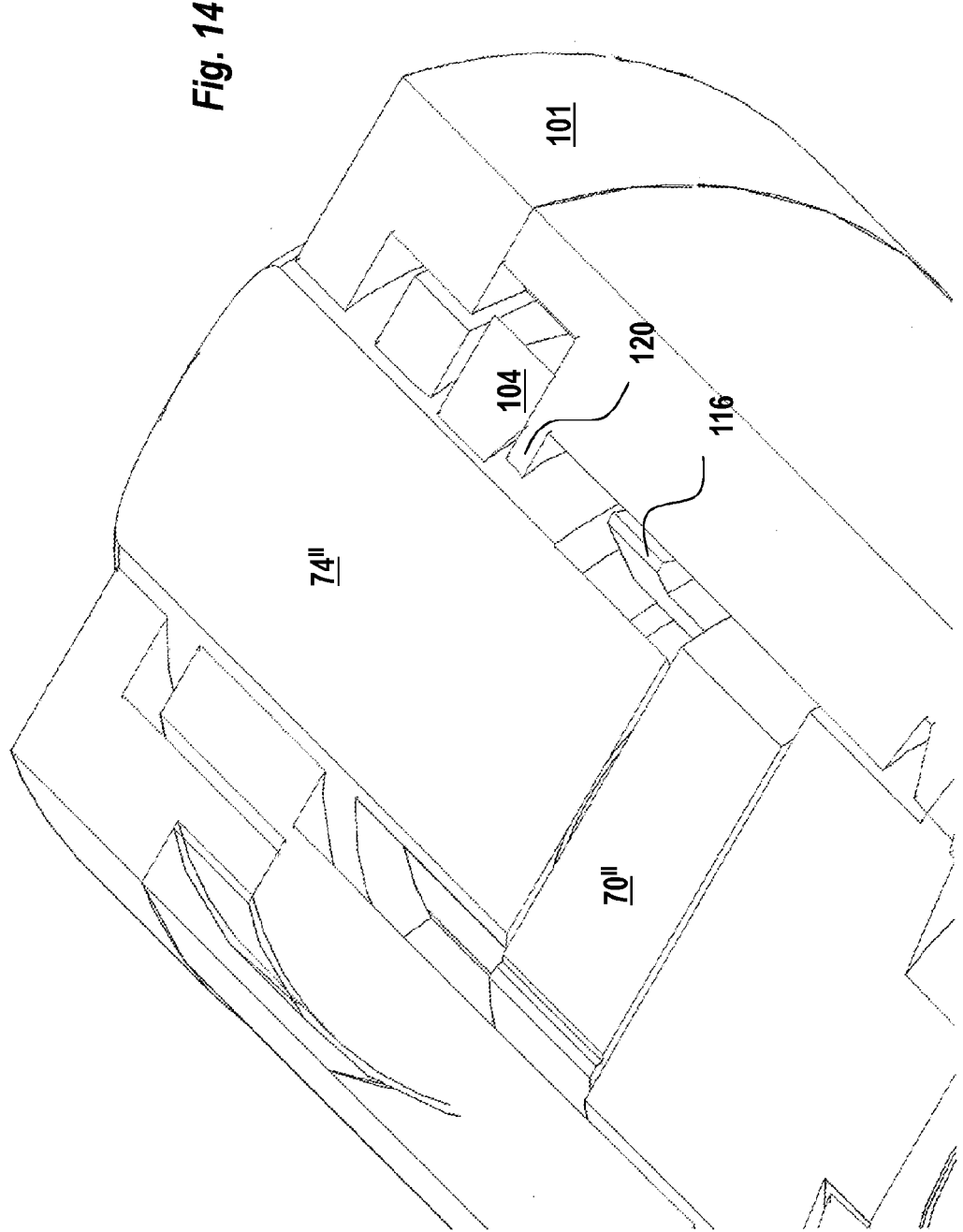

FIGS. 8 to 14 show a second embodiment of the present invention, where FIG. 8 is a perspective view of the medicament delivery device according to the second embodiment of the invention and FIG. 9 is an exploded view of the device of FIG. 8. FIGS. 10-12 are detailed views of some components of the device of FIG. 8. In FIG. 10, the connection member 46" is shown when connected to the spring-loaded plunger rod 34". In FIG. 13 is shown when the activation member 101 is in an inactive position wherein the actuator 74" is prevented from engaging the medicament delivery drive unit. In FIG. 14 is shown when the activation member 101 is in an active position and wherein the actuator 74" is engaging the medicament delivery drive unit.

Figure 15:
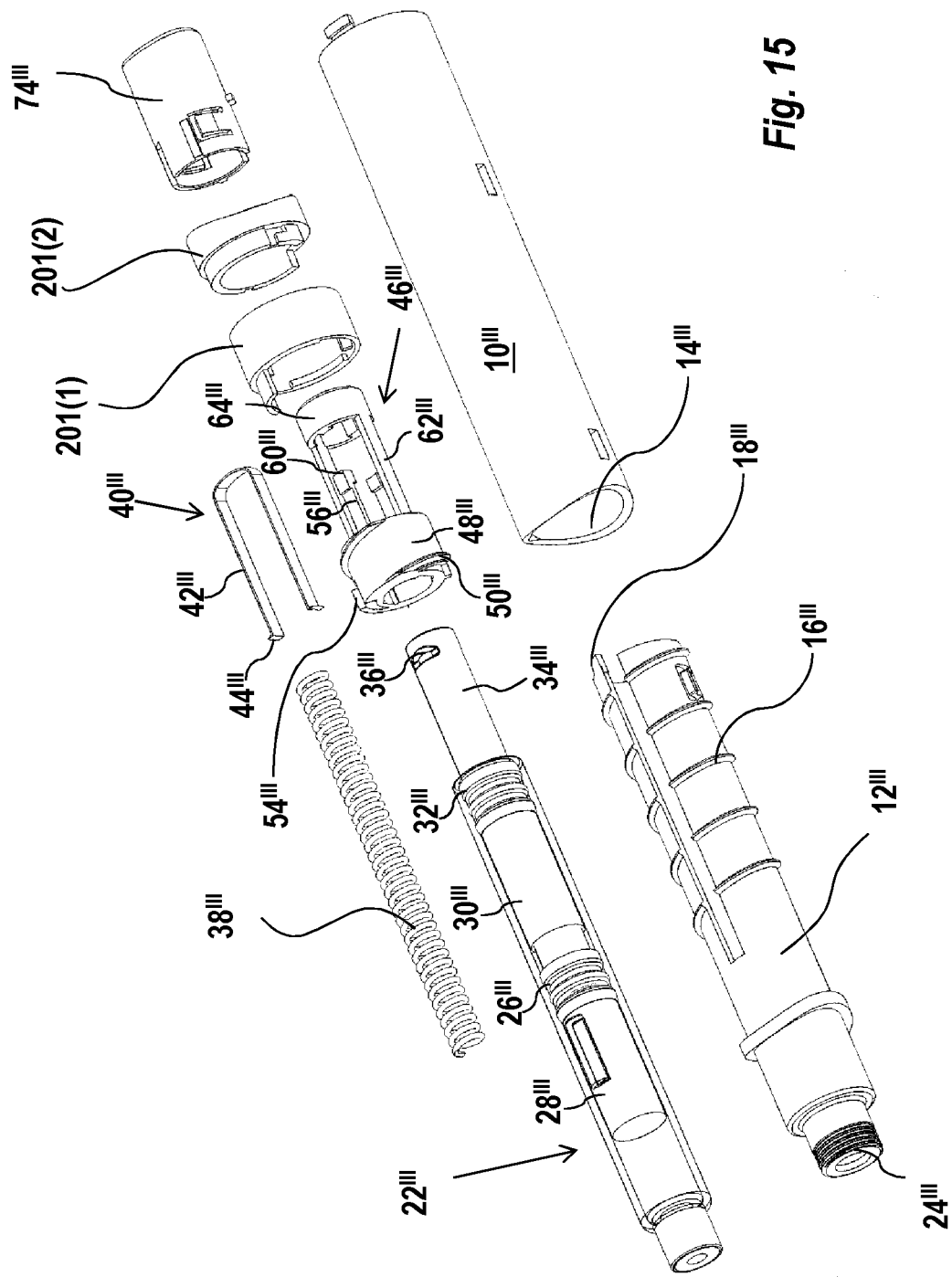
FIG. 15 is an exploded view of a medicament delivery device according to a third embodiment of the invention.
Figure 16:
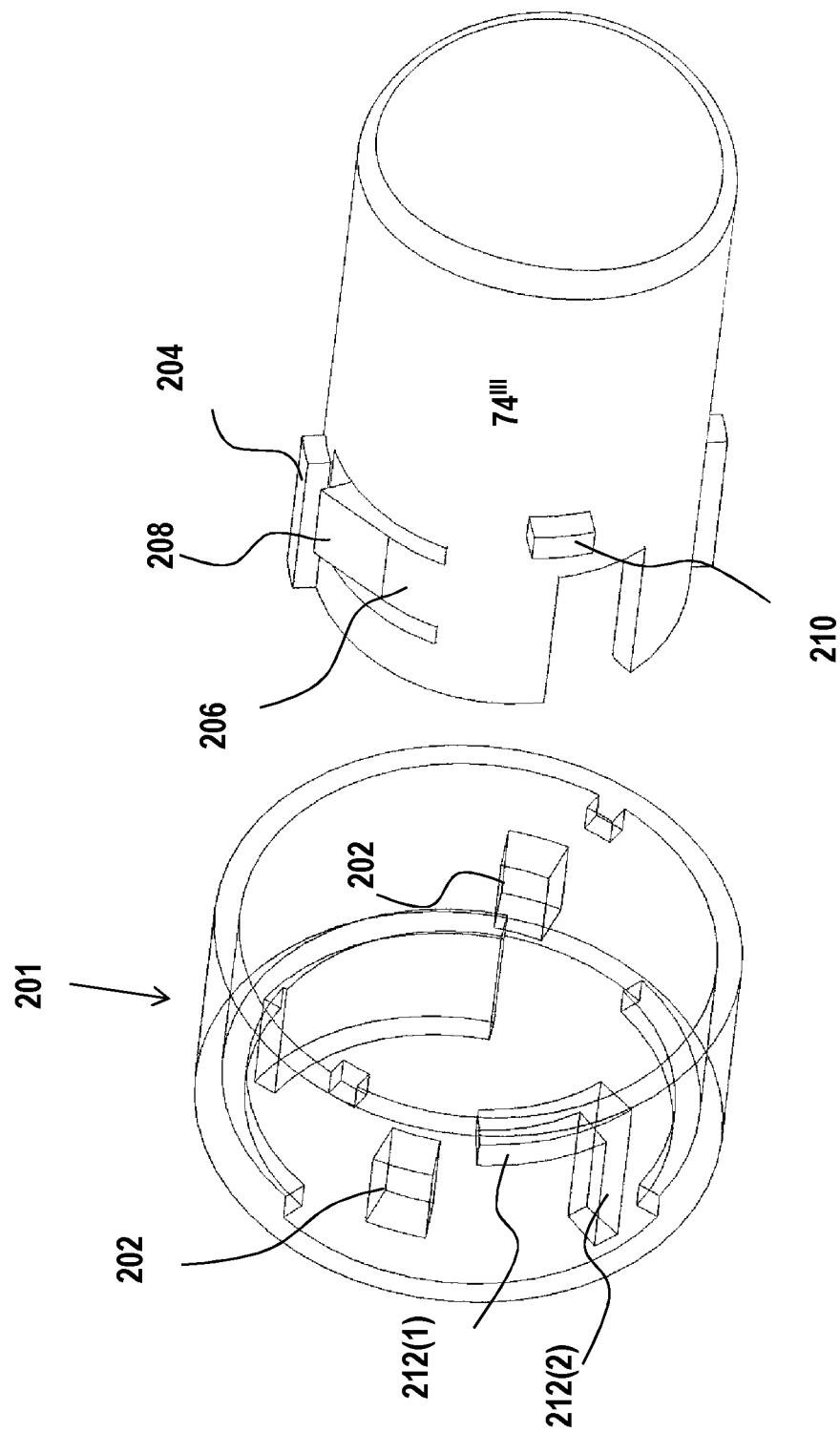
FIGS. 16-23 are detailed views of different functional positions of the device of FIG. 15.
Figure 17:
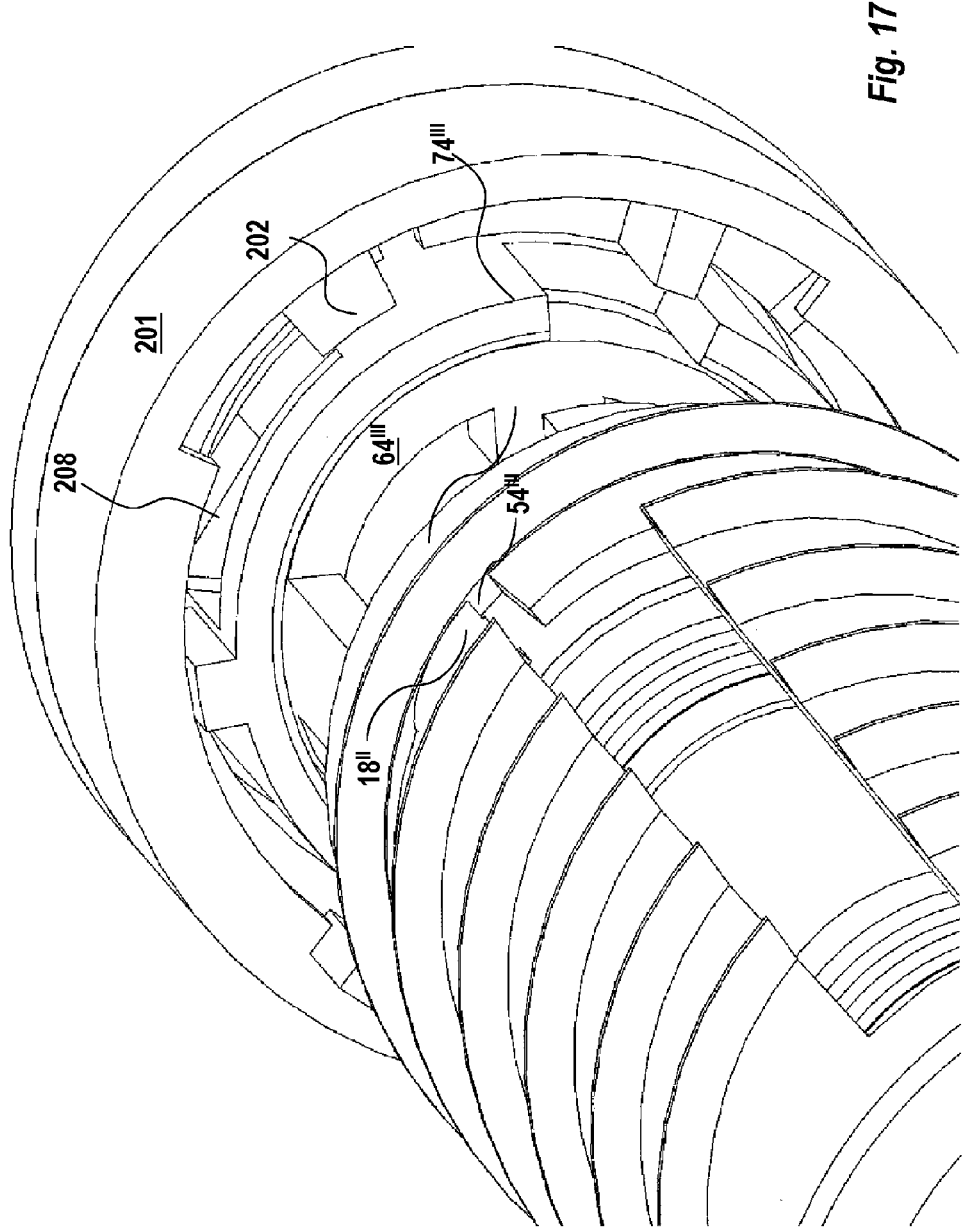
Figure 18:
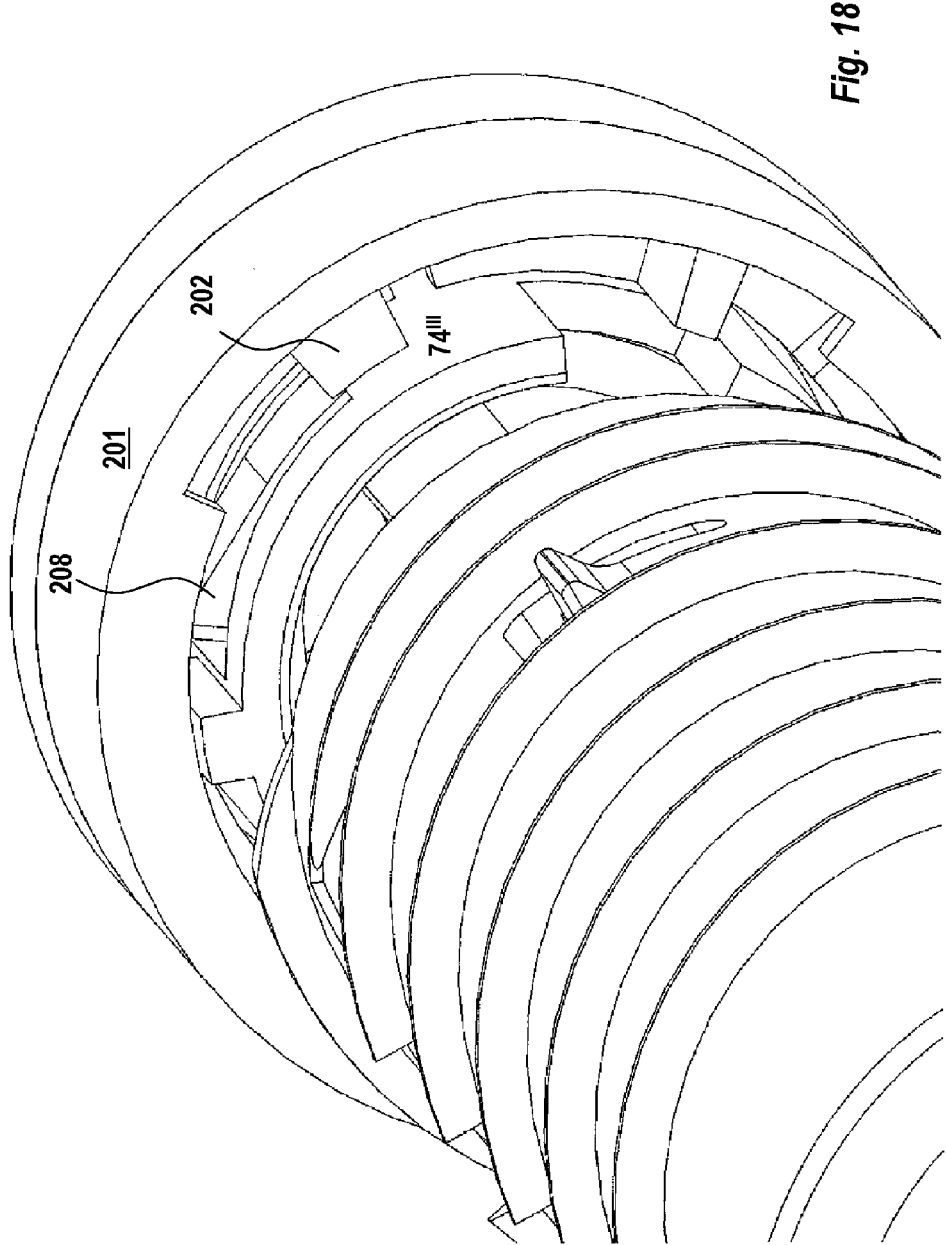
Figure 19:
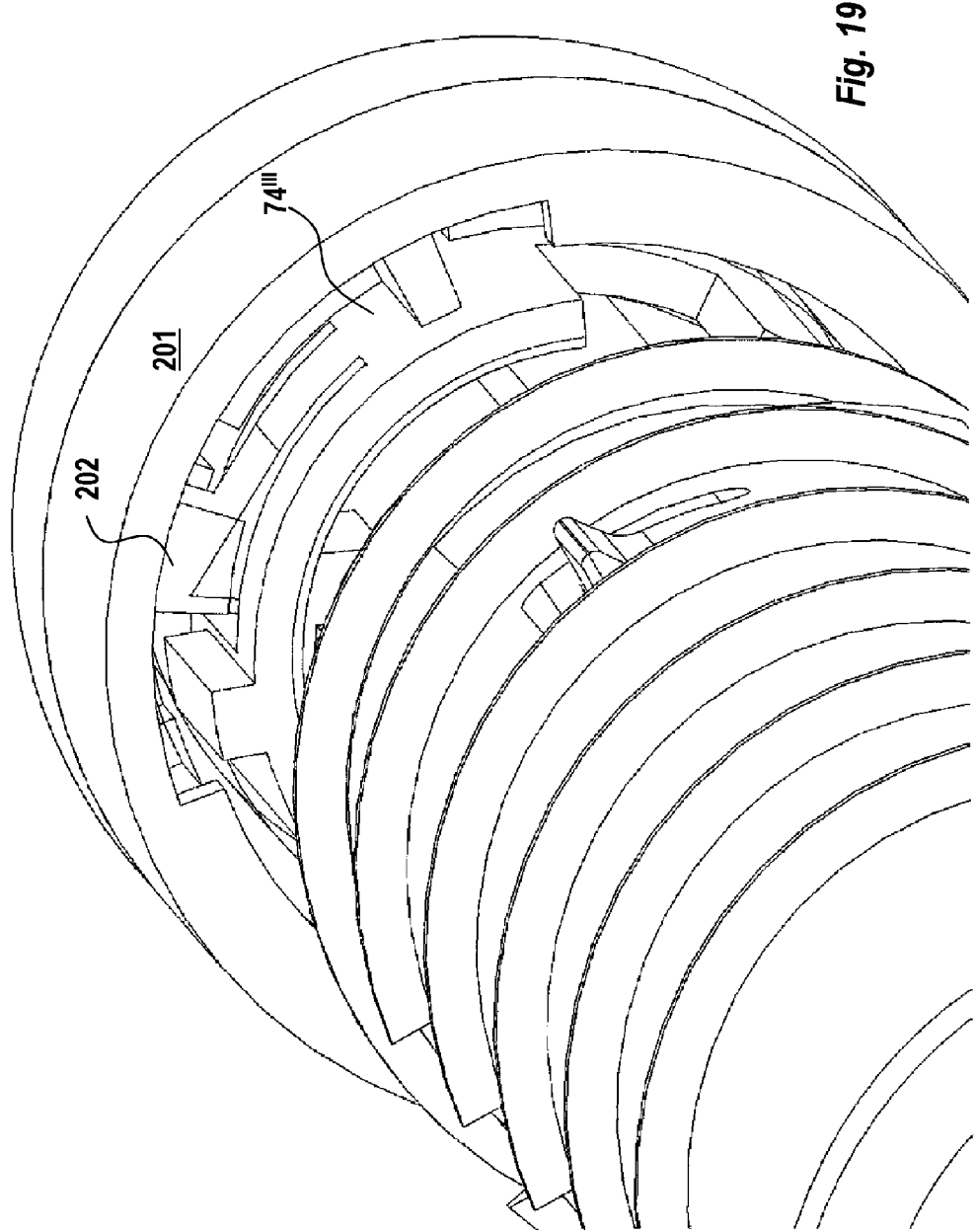
Figure 20:
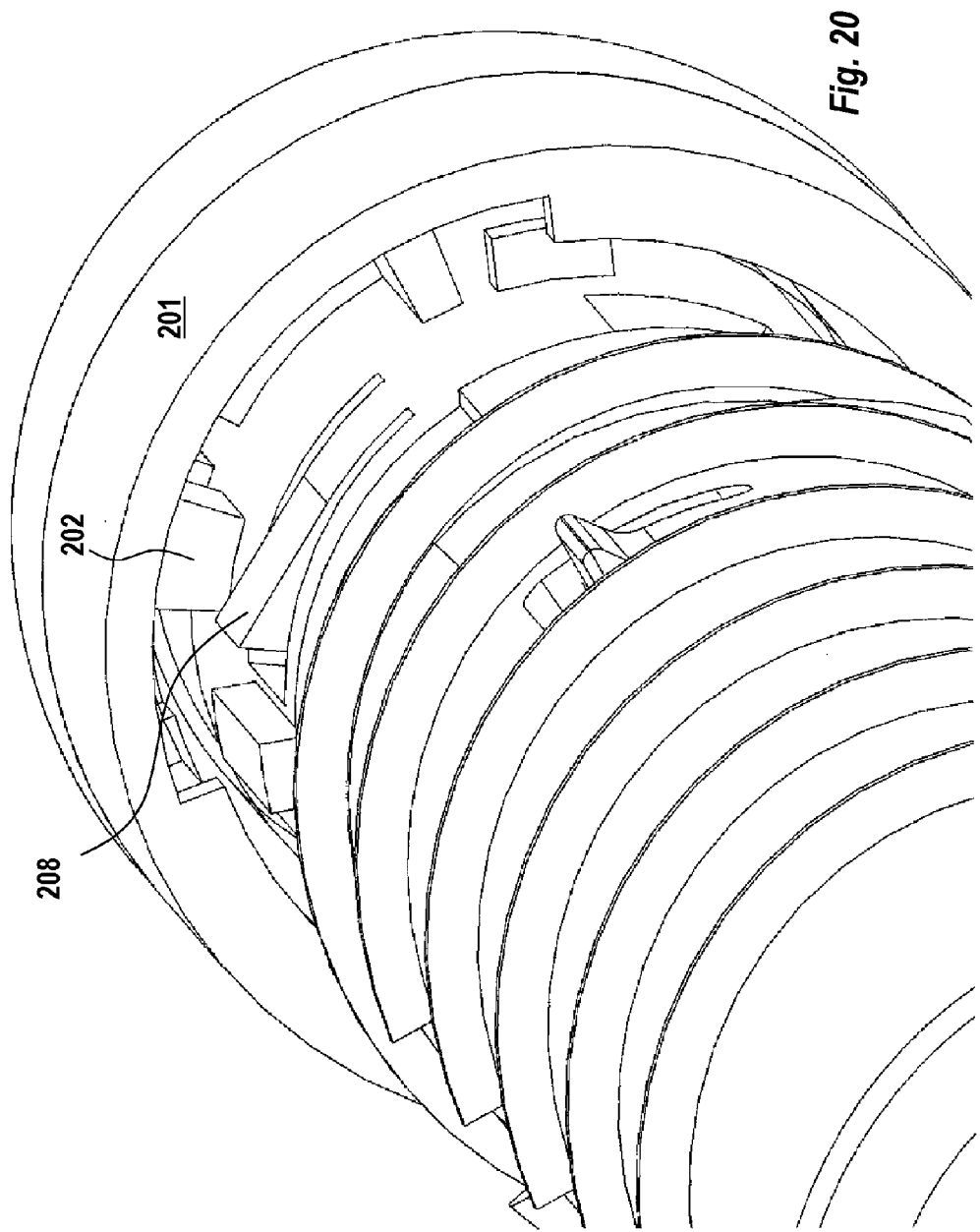
Figure 21:
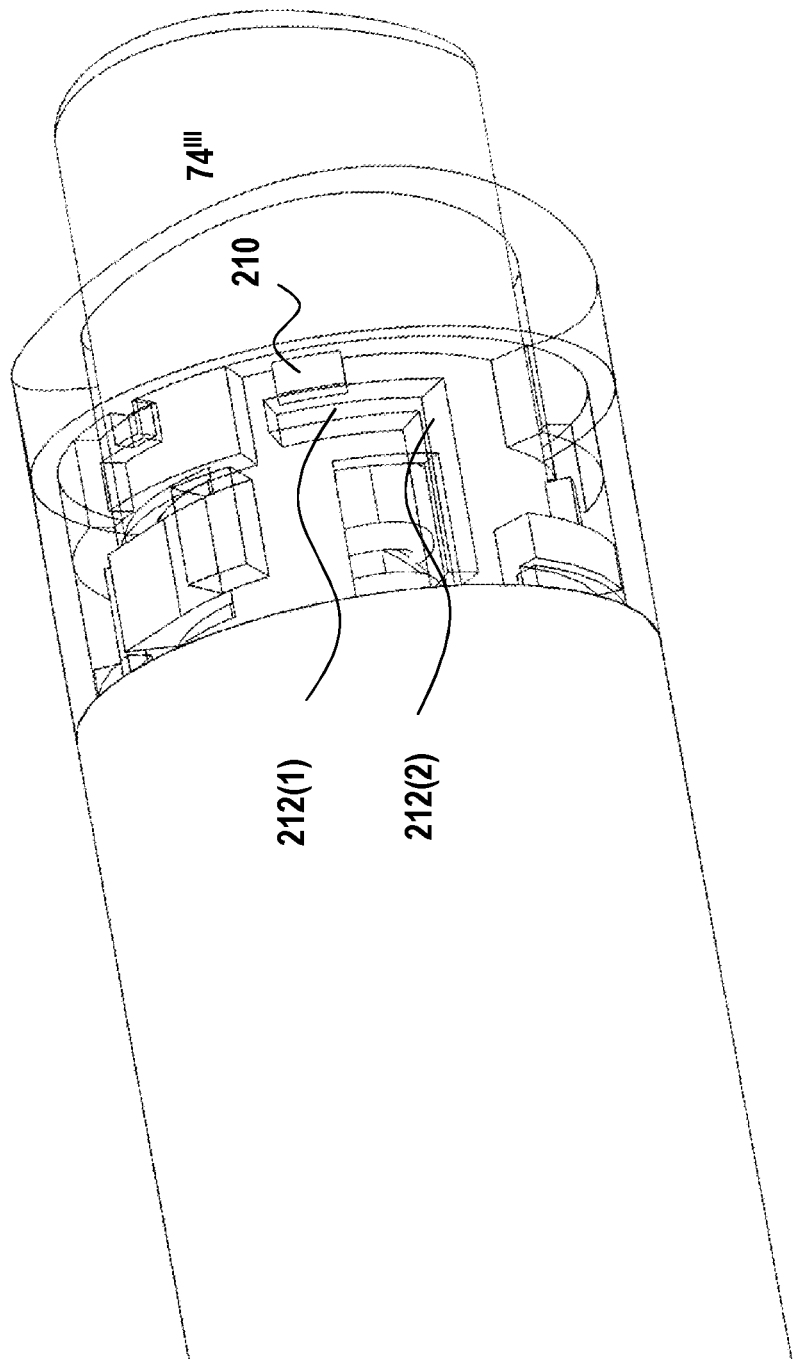
Figure 22:
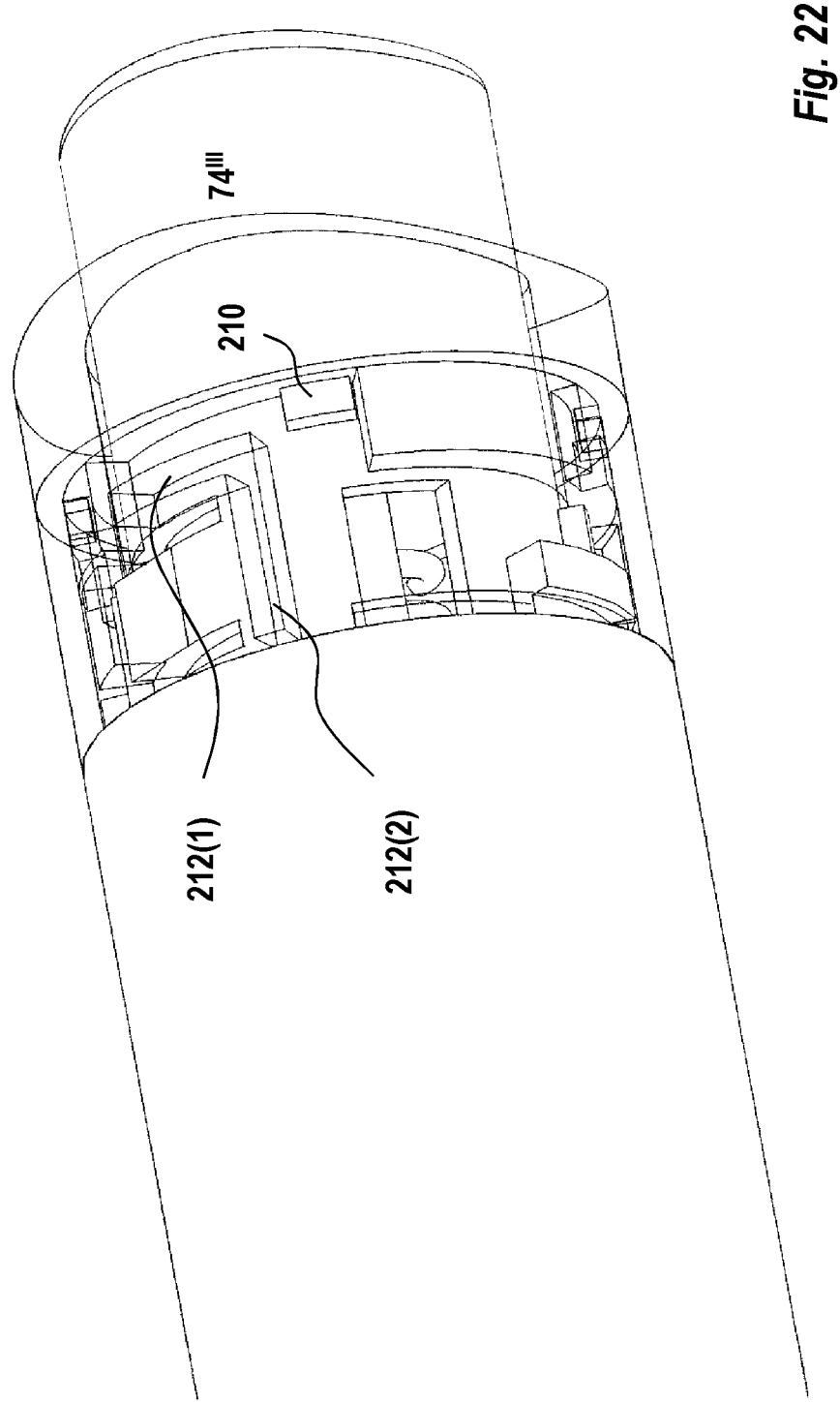
Figure 23:
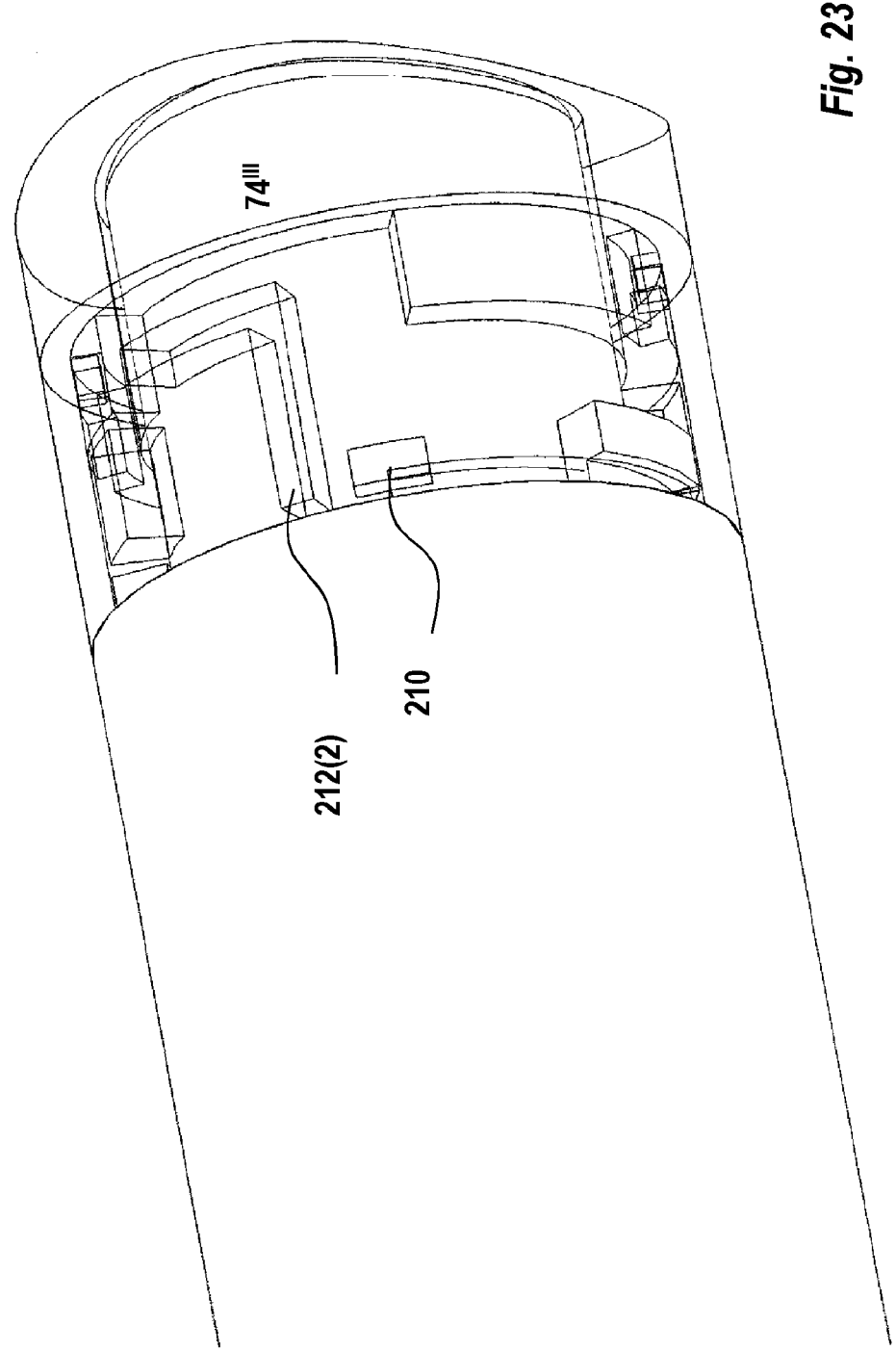

FIGS. 15 to 23 show a third embodiment of the present invention, where FIG. 15 is an exploded view of the third embodiment of the present invention. In FIG. 16 is shown a detailed perspective view of the actuator 74''' and of the activation member 201. In FIG. 17 is shown when the proximal housing part is in a retracted position and the medicament delivery drive unit is still in the first position. In FIG. 18 is shown when the medicament delivery drive unit is in the second position and wherein the activation member 201 is in an inactive position such that the actuator 74''' is prevented from engaging the medicament delivery drive unit. In FIGS. 19 and 22 is shown when the activation member 201 is in an active position. In FIGS. 20 and 23 is shown when the actuator 74''' is engaging the medicament delivery drive unit. In FIG. 21 is shown when the the activation member 201 is in an inactive position such that the actuator 74''' is prevented from engaging the medicament delivery drive unit.

In FIG. 1, a medicament delivery device according to a first embodiment of the invention is shown. The proximal housing part 12 is inserted and interconnected with the distal housing part 10 i.e. the housing parts are in the retracted position. Although not shown, the proximal housing part is screwed into the distal housing part along an axial direction of the medicament delivery device i.e. the housing parts have been moved relative to one another from an extended position to a retracted position. The proximal end of the proximal housing part is provided with a neck portion 24 having attachment means in the form of screw threads and to which a medicament delivery member is releasably connected. It is to be understood that other types of attachment members can be used, such as bayonet fittings, snap-on clips and the like. The delivery medicament member may be selected from a group consisting of a needle, a mouth or nasal piece, a nebulizer, and a nozzle.

In all three embodiments, see FIGS. 2, 9 and 15, is shown that the assembled medicament delivery device has a body which, in turn, comprises the distal housing part 10; 10"; 10''' and the proximal housing part 12; 12"; 12''' which are screw-connected, i.e. they are connected together by screw means. The connection means between the housing parts comprises threads 14; 14"; 14''' arranged on the inner surface of the distal housing part cooperating with threads 16; 16"; 16''' on the outer surface of the proximal housing part. The proximal housing part 12; 12"; 12''' is arranged with at least one distally or axially directed engagement member 18; 18"; 18''' attached to, or made integral with, a distal end surface of the proximal housing part 12; 12"; 12'''.

Furthermore, in all three embodiments, see FIGS. 2, 9 and 15, is shown that inside the multi-chamber container 22; 22"; 22''', a first axially movable stopper 26; 26"; 26''' is arranged to divide the container into a first chamber or compartment 28; 28"; 28''' and a second chamber or compartment 30; 30"; 30'''. One chamber or compartment is arranged to contain the medicament agent in powder form and the other chamber or compartment is arranged to contain the diluent agent which is to be mixed with the powder medicament during a mixing step. A second axially movable stopper 32; 32"; 32''' is arranged at the distal end of the container for sealing the distal compartment.

In all three embodiments, see FIGS. 2-4, 9, 10, 15 and 17, the medicament delivery drive unit comprises a spring-loaded plunger member 34; 34"; 34''' provided with a hollow space into which a drive spring 38; 38"; 38''' is arranged to spring-load the plunger, a drive spring holder 40; 40"; 40''' configured to partially surround the spring-loaded plunger member, a connection member 46; 46"; 46''' through which said drive spring holder is axially arranged, and an actuator member 70; 70"; 70''' being co-axially slidable on said connection member for holding said spring-loaded plunger rod in a pre-loaded state.

In all three embodiments, see FIGS. 2, 3, 9, 11 and 15, the connection member 46; 46"; 46''' comprises a proximal tubular part 48; 48"; 48''' and a distal tubular part 64; 64"; 64''' connected to each other by two axially extending interconnecting portions 62, 62", 62'''. The proximal tubular part 48; 48"; 48''' comprises an outer circumferential surface, a proximal annular surface and a distal annular surface. The connection member 46; 46"; 46''' further comprises at least one radially flexible arm 56; 56"; 56''' which extends distally from the distal annular surface of the proximal tubular part between the two axially extending interconnecting portions 62; 62"; 62'''. The distal ends of the at least one radially flexible arm 56; 56"; 56''' is arranged with an inwardly directed hook 60; 60"; 60'''. The drive spring holder 40; 40"; 40''' is configured having a generally U-shape with proximally directed legs 42; 42"; 42''' and wherein each leg comprises a radial outwardly extending ledge 44; 44"; 44'''. When the medicament delivery drive unit is assembled, the drive spring 38; 38"; 38''' is compressed between a proximal inner end surface of the plunger member 34; 34"; 34''' and a transversal contact end of the drive spring holder 40; 40; 40''''; the radial outwardly extending ledges 44 are engaged to the proximal annular surface of the proximal tubular part 48; 48"; 48''' for preventing the drive spring holder from being moved in the distal direction by the drive spring; and the actuator member 70; 70"; 70''', which is a ring-shaped member, is arranged surrounding said at least one radially flexible arm 56; 56"; 56''' such that the inwardly directed hook 60; 60"; 60''' is engaged in a corresponding engagement with a cut-out 36; 36"; 36''' on said spring-loaded plunger member to fixate said spring-loaded plunger member relative to said distal housing part.

Further, in all three embodiments, see FIGS. 2, 3, 9, 11 and 15, the connection member 46; 46"; 46''' comprises counteracting connection means 50; 50"; 50''' on the outer circumferential surface of the proximal tubular part 48; 48"; 48'''. Said counteracting connection means 50; 50"; 50''' in the form of a thread segment is arranged to cooperate with the connection means 14; 14"; 14''' in the form of threads on the inner surface of the distal housing part, such that when the medicament delivery drive unit is in the first position, the medicament delivery drive unit is fixed in relation to the distal housing part and the proximal outer end of the spring-loaded plunger member 34; 34"; 34''' is arranged to abut the second axially movable stopper 32; 32"; 32'''. Then, when the distal and the proximal housing parts move relative to one another from the extended position to the retracted position, the medicament delivery drive unit acts on said multi-chamber container i.e. the second axially movable stopper 32; 32"; 32''' is pressed against the proximal outer end of the spring-loaded plunger member 34; 34"; 34''' whereby said at least two agents are mixed and thereby obtaining the reconstituted medicament.

Further, in all three embodiments, see FIGS. 5, 10 and 15, the connection member 46; 46"; 46''' further comprises at least one proximally or axially directed counteracting engagement member 54; 54"; 54 arranged to interact with said at least one distally or axially directed engagement member 18; 18"; 18''' of said proximal housing part after the reconstituted medicament is obtained, such that the medicament delivery drive unit is moved from the first position to the second position.

In the first embodiment, see FIGS. 3-6, the distal tubular part 64 is arranged with an end surface 66. On said end surface 66, two inwardly directed hooks 68 are attached and arranged to engage or secure a counteracting compression spring 78 which is arranged to cooperate with the actuator 74. The actuator 74 is arranged as a push button extending through an opening at the distal end of the distal housing part 10. The actuator 74 is arranged to be pressed or pushed in the axial direction into the distal housing part. The pushing or pressing of the actuator is counteracted by the counteracting compression spring 78, which is fastened or secured by the inwardly directed hooks 68 on the connection member 46. Further, the actuator 74 and the activation member 74 are configured to be integral as a single component, hereinafter called the actuation means and which will use the common reference number 74. The actuation means 74 comprises through-holes 81 on its outer circumferential surface such that a rotational movement of the actuation means 74 in relation to the distal housing part is prevented by the interaction between said through-holes 81 and flexible radial inwardly directed protrusions (not shown) on the inner surface of the distal housing part. Further, the actuation means 74 comprises slits 80 on its outer circumferential surface such that a longitudinal or axial movement of the actuation means 74 in relation to the distal housing part is limited by the interaction between said slits 80 and the flexible radial inwardly directed protrusions (not shown) on the inner surface of the distal housing part. The through holes 81 and the slits 80 are interconnected to each other by a transversal guide groove (not shown) on the outer circumferential surface of the actuation means, the function thereof will be explained below.

The function of the device as disclosed in the first embodiment is as follows. When the device is delivered to a user, the first thing is to attach a medicament delivery member. For example an injection needle is attached to the neck portion 24 of the proximal housing part 12. Then the user has to mix the medicament agent with the diluent agent i.e. a mixing step or sequence. The user then engages the two housing parts 10 and 12 and screw-connects them towards each other. In this first embodiment, this causes the proximal housing part 12 to be axially moved inside the distal housing part 10 due to the connection by the threads 14, 16, i.e. the proximal and distal housing parts are moved towards each other from the extended position to the retracted position in order to urge the spring-loaded plunger into the medicament container i.e. the second axially movable stopper 32 is pressed against the proximal outer end of the spring-loaded plunger member 34 whereby said at least two agents are mixed, thereby obtaining the reconstituted medicament. During the mixing step or sequence, the actuator member 70 is coaxially arranged on the arms 56 such that the hooks 60 are in engagement with the cut-outs 36 of the spring-loaded plunger member 34, i.e. the driver spring is kept in a compressed state during the mixing step or sequence. Also during the mixing step or sequence, the actuation means 74 is prevented to be pressed into the distal housing part due to the interaction between the through-holes 81 on the circumferential outer surface of the actuation means and the flexible radial inwardly directed protrusions on the inner surface of the distal housing part 12. As shown in FIG. 6, after the mixing step is performed, the distally or axially directed engagement member 18 of the proximal housing part is now in contact with the counteracting engagement member 54 of the connection member 46. Thus, as shown in FIGS. 5 and 6, the medicament delivery drive unit is in the first position wherein the actuator member 70 is positioned spaced from the actuation means 74 i.e. the actuator member 70 is positioned at a predetermined distance from the actuation means 74 such that release of said spring-loaded plunger is prevented. A further turning of the proximal housing part 12 in relation to the distal housing part 10 causes the connection member 46 also to be distally displaced due to the interaction between the thread segment 50 and the threads 14 of the distal housing part. The distal tubular part 64 of the connection member 46 is then moved into the actuation means 74, such that the outer circumferential surface of the distal tubular part 64 forces the flexible radial inwardly directed protrusions (not shown) on the inner surface of the distal housing part to move radial outwardly. Thus, the actuation means 74 may be rotated in relation to the distal housing part from the inactive position via the transversal guide groove to the active position. In the inactive position the actuation means is prevented from being pressed into the distal housing part, due to the interaction between the flexible radial inwardly directed protrusions (not shown) on the inner surface of the distal housing part and the through-hole 81 on the outer circumferential surface of the actuation means. In the active position the flexible radial inwardly directed protrusions (not shown) on the inner surface of the distal housing part interact with the slits 80 to allow axial movement of the actuation means 74. Moreover, when the medicament delivery drive unit is moved from the first position to the second position, the connection member 46 is moved to a position wherein the actuator member 70 is closer to the actuation means 74 (see FIG. 7).

Thereafter, when the mixing step has been completed, the medicament has been reconstituted, the medicament delivery drive unit has been moved from the first position to the second position, and the actuation means has been rotated from the inactive position to the active position; the device is prepared to be activated by pressing the actuation means 74 into the distal housing part.

Now delivery of the reconstituted medicament may be performed. The proximal end of the device, with the medicament delivery member, is positioned at the dose delivery site, which could be an injection site if an injection needle is used, at which site a penetration is performed manually. The user then operates the actuation means 74 by pressing it axially towards the proximal direction. This in turn causes the actuator member 70 to be proximally moved due to the contact between the actuation means 74 and the actuator member 70. The proximal movement of the actuator member 70 causes it to slide along the arms 56. The arms 56 thereafter resiliently returns back to its resting or upright position, i.e. the arms are now free to move in the outwardly radial direction, which causes the hooks 60 to move out of contact with its resilient engagement with the cut-outs 36 of the spring-loaded plunger rod 34. This in turn releases the spring-loaded plunger rod 34 to move in the proximal direction due to the force of the compressed drive spring 38. The movement of the spring-loaded plunger rod 34 forces the stoppers 26, 32 to move proximally inside the container 22 and thereby expel the reconstituted medicament through the medicament delivery member. When the stoppers 26, 32 have reached their end position, i.e. the proximal end position, inside the medicament container 22, the medicament delivery operation is completed.

The medicament delivery device is further arranged with a technical feature to indicate and thereby inform the user when the delivery operation is completed. In response to a signal indicative of the completed delivery operation, the technical feature is arranged to generate an audible signal. At the end of the medicament delivery sequence, the distal end of the spring-loaded plunger rod 34 is moved out of contact with the proximal end of the arms 42 of the drive spring holder 40. Thereby the arms 42 and thus the ledges 44 are free to move radially inwards, whereby the ledges 44 move out of contact with the connection member 46. Due to a remaining force on the drive spring 38 acting on the drive spring holder 40, the latter is moved in the distal direction until the drive spring holder contacts the end surface 66 of the actuator device 46. When the spring holder strikes the end surface 66 of the actuator device 46, an audible signal is produced. The user may now remove the device from the delivery site and discard it in a safe manner.

It is also to be understood that other types of movement may be performed after mixing in order to move the medicament delivery drive unit from the first position to the second position. For example, the housing parts may be arranged slidable in relation to each other.

Further, the actuation means may have other designs than a push button and may be positioned in other areas of the body than the distal end. For example the actuation means may be a member arranged on the side of the body and being slidable in the longitudinal direction of the device.

In the second embodiment, see FIGS. 9-14, the actuator 74" and the activation member 101 are configured to be separated components. The activation member 101 being in the form of a generally cylindrical locking ring is arranged at the distal end of the distal housing part 12" and is attached to the latter such that it is rotatable. The proximal end surface of the activation member 101 is arranged with arms 102 (see FIG. 12) that extend generally in the circumferential direction of activation member 101. The arms 102 are radially flexible, i.e. flexible in the radial direction. The free ends of the arms 102 are provided with radial inwardly directed protrusions 104. These protrusions 104 fit into slits 106 which are arranged in a ring-shaped housing part 108 of the distal housing part 12" (see FIG. 11). The actuator 74" is arranged with axially extending ledges 110 on its outer surface fitting into axially extending grooves 112 arranged on the inner surface of the ring-shaped housing part 108 (see FIG. 11). Furthermore, the actuator 74" is arranged with arms 114 extending in the circumferential direction, and being flexible in the radial direction. The outer surface of the arms 114 are arranged with protrusions 116 having a general wedge-shape, the function thereof will be explained as below. Furthermore, the distal tubular part 64" of the connection member 46" has a chamfered transition surface 118.

FIG. 13 shows when the activation member 101 is in the inactive position wherein the actuator 74" is prevented from being pressed into the distal housing part and FIG. 14 shows when the activation member 101 is in the active position and wherein the actuator 74" is pressed into the distal housing part. The second embodiment is intended to function as follows. When the device is delivered to the user the agents within the container have to be mixed in the same manner as described in conjunction with the first embodiment. However, the actuator 74" is prevented from being pressed into the distal housing part by the interaction between the protrusions 116 of the actuator 74" and a circumferential ledge 120 on the inner surface at the distal end of distal housing part 12" (FIG. 13). Thus, the circumferential ledge 120 forms a mechanical stop for an axial movement of the actuator 74" thereby blocking the actuator 74" to be moved towards the proximal end of the device. Furthermore, when the activation member 101 is in the inactive position as shown in FIG. 13, the activation member 101 is prevented from being displaced i.e. is prevented to rotate, since the outer circumferential surface of the second tubular member 64" is abutting the inner surface of the arms 114 and the protrusions 116 on the outer surface of the arms 114 are obstructing the radial inwardly directed protrusions 104 of the activation member. However, when the agents within the container have been mixed and the medicament delivery drive unit has been moved from the first position to the second position after completion of the mixing sequence or step as described above for the first embodiment, the second tubular part 64" of the connection member 46" has been moved distally such that the outer circumferential surface of the second tubular part 64" of the connection member 46" is no longer abutting the inner surface of the arms 114 of the actuator 74". Thereby it is possible to turn the activation member 101 to the active position whereby the protrusions 104 of the activation member 101 engages or contacts with the wedge-shaped protrusions 116 of the actuator 74". When the activation member 101 is rotated, the protrusions 116 are moved radially inwards causing the protrusions 116 to move out of contact with the ledge 120 (see FIG. 14). The activation member is now in the active position whereby the actuator 74" is no longer blocked. The actuator 74" is now able to be pushed or pressed axially towards the proximal end of the device in order to initiate a medicament delivery, whereby the protrusions 116 are able to pass the ledge 120 without being blocked. Then, the movement of the actuator 74" towards the proximal end of the device causes the actuator member 70" to be moved in the same manner as described above for performing a medicament delivery.

In the third embodiment, see FIGS. 15 to 23, the actuator 74''' and the activation member 201 are also configured to be separated components. The activation member 201 being in the form of a generally cylindrical locking ring is arranged at the distal end of the distal housing part 12''' and is attached to the latter such that it is rotatable. The activation member 201, in the third embodiment is shown as two components 201(1) and 201(2), see FIG. 15. However, this is merely due to production and assembling aspects. When assembled, these two components function as a single component. The activation member 201 comprises on its inner circumferential surface inwardly directed protrusions 202 and ledges 212. The ledges 212 comprise a first ledge segment 212(1) having a generally circumferential extension and a second ledge segment 212(2) having a generally axial extension (see FIG. 16). Further the actuator 74''' comprises on its outer circumferential surface axially directed ledges 204, a set of outwardly directed knobs or protrusions 210, and flexible arms 206 extending in the circumferential direction. The outer surface of the arms 206 are provided with wedge-shaped protrusions 208. The ledges 204 cooperate with axially extending grooves (not shown) on the inner surface of the distal housing part 12''' in the same manner as with the second embodiment, and the protrusions 210 are arranged to interact with ledge segments 212(1).

In FIG. 21, is shown when the actuator 74''' is prevented from being pressed into the distal housing part because the activation member 201 is in the inactive position wherein the first ledge segment 212(1) is positioned proximal to the protrusion 210 of the actuator 74'''. Furthermore, when the activation member 201 is in the inactive position as shown in FIG. 17, the activation member 201 is prevented from being displaced i.e. is prevented to rotate, since the outer circumferential surface of the second tubular member 64''' is abutting the inner surface of the arms 206, and the protrusions 208 on the outer surface of the arms 206 are obstructing the radial inwardly directed protrusions 202 of the activation member. However, when the agents within the container have been mixed and the medicament delivery drive unit has been moved from the first position to the second position after completion of the mixing sequence or step as described above for the first embodiment, the second tubular part 64''' of the connection member 46''' has been moved distally such that the outer circumferential surface of the second tubular part 64''' of the connection member 46''' is no longer abutting the inner surface of the arms 206 of the actuator 74''', FIG. 18. Thereby it is possible to turn the activation member 201 to the active position whereby the protrusions 202 of the activation member 201 engages or contacts with the wedge-shaped protrusions 208 of the actuator 74'''. When the activation member 201 is rotated, the protrusions 202 push the arms 206 radially inwards, FIG. 19. Further, the turning of the activation member 201 causes also the ledge segment 212(1) to be moved out of line in relation to the protrusions 210 of the actuator 74''', FIG. 22. The activation member 201 is now in the active position whereby the actuator 74''' is no longer blocked, FIG. 22. The actuator 74''' is now able to be pushed or pressed axially towards the proximal end of the device in order to initiate a medicament delivery, see FIGS. 20 and 23. Then, the movement of the actuator 74''' towards the proximal end of the device causes the actuator member 70''' to be moved in the same manner as described above for performing a medicament delivery. After performed medicament delivery the device may be discarded in a safe way.

The medicament delivery device of any one of the embodiments as described above is an injection device, being preferably an auto-injector, wherein the auto-injector is an injection device having an spring-loaded plunger rod.

It is to be understood that the embodiments described above and shown in the drawings are to be regarded only as non-limiting examples of the invention and that it may be modified in many ways within the scope of the patent claims.

The invention claimed is:

1. A medicament delivery device for obtaining and delivering a reconstituted medicament, comprising:
    a proximal housing part configured to accommodate a multi-chamber container containing at least two agents;
    a distal housing part connected to the proximal housing part;
    a medicament delivery drive unit accommodated in the distal housing part, wherein the proximal housing part and the distal housing part are configured to be movable relative to each other from an extended position to a retracted position, whereby the medicament delivery drive unit acts on the multi-chamber container for mixing the at least two agents and thereby obtains the reconstituted medicament; and
    an actuation mechanism provided on the distal housing part and including an actuator provided to engage the medicament delivery drive unit when operated by a user for delivering the reconstituted medicament;

wherein the medicament delivery drive unit is mounted in the distal housing part so as to be directly moved, by the proximal housing part when the proximal and distal housing parts are moved from the extended position to the retracted position, from a first position spaced from the actuator to a second position in which the medicament delivery drive unit can be engaged by the actuator; and the actuation mechanism further includes an activation member that is displaceable between an inactive position, in which the actuator is prevented from engaging the medicament delivery drive unit, and an active position, in which the actuator is able to engage the medicament delivery drive, whereby the actuator is capable of interacting with the medicament delivery drive unit to perform a delivery of the reconstituted medicament only in the active position of the activation member and in the second position of the medicament delivery drive unit.

2. The medicament delivery device of claim 1, wherein the actuator is configured to be axially movable in relation to the distal housing part in a direction toward the medicament delivery drive unit.

3. The medicament delivery device of claim 1, wherein the medicament delivery drive unit comprises a spring-loaded plunger member having a hollow space into which a drive spring is arranged to spring-load the plunger, a drive spring holder configured to partially surround the spring-loaded plunger member, a connection member through which the drive spring holder is axially arranged, and an actuator member co-axially slidable on the connection member for holding the spring-loaded plunger member in a pre-loaded state.

4. The medicament delivery device of claim 3, wherein the multi-chamber container comprises a first axially movable stopper configured to divide the multi-chamber container into a first compartment and a second compartment, and a second axially movable stopper for sealing the second compartment.

5. The medicament delivery device of claim 4, wherein the connection member comprises a proximal tubular part and a distal tubular part connected to each other by two axially extending interconnecting portions, and at least one radially flexible arm extending distally from a distal annular surface of the proximal tubular part between the two axially extending interconnecting portions.

6. The medicament delivery device of claim 5, wherein the at least one radially flexible arm is configured with an inwardly directed hook configured to be engaged with a cutout on the spring-loaded plunger member to fix the spring-loaded plunger member relative to the distal housing part by the actuator member which is arranged surrounding the at least one radially flexible arm.

7. The medicament delivery device of claim 6, wherein the drive spring holder has a generally U-shape with proximally directed legs, and each leg comprises a radial outwardly extending ledge, such that when the medicament delivery drive unit is assembled, the drive spring is compressed between a proximal inner end surface of the plunger member and a transversal contact end of the drive spring holder.

8. The medicament delivery device of claim 7, wherein the radial outwardly extending ledges are engaged to a proximal annular surface of the proximal tubular part for preventing the drive spring holder from being moved in the distal direction by the drive spring.

9. The medicament delivery device of claim 8, wherein the connection member further comprises counteracting connection devices on the outer circumferential surface of the proximal tubular part arranged to cooperate with a connection device on the inner surface of the distal housing part, such that when the medicament delivery drive unit is in the first position, the medicament delivery drive unit is fixed in relation to the distal housing part and a proximal outer end of the spring-loaded plunger member is arranged to abut the second axially movable stopper, and when the distal and proximal housing parts are moved relative to one another from the extended position to the retracted position, the second axially movable stopper is pressed against the proximal outer end of the spring-loaded plunger member, whereby the at least two agents are mixed.

10. The medicament delivery device of claim 9, wherein the connection member further comprises at least one proximally or axially directed counteracting engagement member arranged to interact with at least one distally or axially directed engagement member of the proximal housing part after the at least two agents are mixed, such that the medicament delivery drive unit is moved from the first position to the second position.

11. The medicament delivery device of claim 10, wherein the distal housing part and the proximal housing part are configured to be screw-connected together to move toward each other.

12. The medicament delivery device of claim 1, wherein the actuator and the activation member are integrally configured as a single component.

13. The medicament delivery device of claim 12, wherein the actuation mechanism further comprises flexible blocking members configured to interact with both the distal housing part and the medicament delivery drive unit when the medicament delivery drive unit is in the first position and the activation member is in the inactive position, such that the activation member is prevented from displacement between the inactive position and the active position.

14. The medicament delivery device of claim 13, wherein the flexible blocking members are configured to be free of interaction with both the distal housing part and the medicament delivery drive unit when the medicament delivery drive unit is in the second position and the activation member is in the active position.

15. The medicament delivery device of claim 1, wherein the actuator and the activation member are configured as separate components.

16. The medicament delivery device of claim 15, wherein the actuator comprises flexible blocking members configured to be releasably engaged to the distal housing part and to interact with the activation member.

17. The medicament delivery device of claim 16, wherein the activation member is configured to interact with the medicament delivery drive unit when the medicament delivery drive unit is in the first position and the activation member is in the inactive position, such that the activation member is prevented from displacement between the inactive position and the active position.

18. The medicament delivery device of claim 17, wherein the activation member comprises counteracting flexible blocking members configured to interact with the flexible blocking members when the medicament delivery drive unit is in the second position and the activation member is in the active position, such that the flexible blocking members are disengaged from the distal housing part.

19. The medicament delivery device of claim 1, wherein the proximal housing part has a neck portion at which the medicament container is arranged to abut.

20. The medicament delivery device of claim 19, further comprising a medicament delivery member releasably connected to the neck portion, wherein the medicament delivery member is selected from a group consisting of a needle, a mouth or nasal piece, a nebulizer, and a nozzle.

21. The medicament delivery device of claim 1, wherein the device is an injection device.

* * * * *